(12) United States Patent
Kavarana et al.

(10) Patent No.: US 10,384,997 B2
(45) Date of Patent: Aug. 20, 2019

(54) BIO-STABLE CANNABINOID COMPOUNDS AND METHODS FOR ENHANCING THEIR PHYSIOLOGICAL CONCENTRATION

(71) Applicant: Teewinot Technologies Limited, Dublin (IE)

(72) Inventors: Malcolm J. Kavarana, Fairfax, VA (US); Richard C. Peet, Washington, DC (US); Jeffrey M. Korentur, Tampa, FL (US)

(73) Assignee: Teewinot Technologies Limited, Dublin (IE)

( * ) Notice: Subject to any disclaimer, the term of this patent is extended or adjusted under 35 U.S.C. 154(b) by 0 days.

(21) Appl. No.: 15/813,358

(22) Filed: Nov. 15, 2017

(65) Prior Publication Data
US 2018/0201560 A1    Jul. 19, 2018

Related U.S. Application Data

(60) Provisional application No. 62/422,352, filed on Nov. 15, 2016.

(51) Int. Cl.
| | |
|---|---|
| *C07C 43/23* | (2006.01) |
| *A61P 25/00* | (2006.01) |
| *C12N 9/02* | (2006.01) |
| *C07C 65/28* | (2006.01) |
| *C12P 7/22* | (2006.01) |

(52) U.S. Cl.
CPC ............. *C07C 43/23* (2013.01); *A61P 25/00* (2018.01); *C07C 65/28* (2013.01); *C12N 9/0004* (2013.01); *C12P 7/22* (2013.01); *C12Y 121/03008* (2015.07); *C07C 2601/16* (2017.05)

(58) Field of Classification Search
CPC .................................................. C07C 43/23
USPC ........................................................ 514/719
See application file for complete search history.

(56) References Cited

U.S. PATENT DOCUMENTS

2016/0053220 A1    2/2016    Peet et al.

FOREIGN PATENT DOCUMENTS

| WO | WO-2008107879 A1 * | 9/2008 | ............. C07C 43/23 |
|---|---|---|---|
| WO | WO-2008107879 A1 | 9/2008 | |
| WO | WO-2014134281 A1 | 9/2014 | |
| WO | 2018091551 | 5/2018 | |

OTHER PUBLICATIONS

"International Application Serial No. PCT/EP2017/079361, International Search Report dated Jan. 17, 2018", 5 pgs.
"International Application Serial No. PCT/EP2017/079361, Written Opinion dated Jan. 17, 2018", 8 pgs.
Adele, Thomas, et al., "6"-Azidohex-2"-yne-cannabidiol: a potential neutral, competitive cannabinoid CB1 receptor antagonist", European Journal of Pharmacology, vol. 487, No. 1-3, (Mar. 8, 2004), 213-221.
Grotenhermen, Franjo, et al., "Even High doses of Oral Cannabidiol Do Not Cause THC-Like Effects in Humans: Comment on Merrick et al. Cannabis and Cannabinoid Research 2016;1(1)102-112; DOI: 10.1089/can.2015.0004", Cannabis and Cannabinoid Research, vol. 1.1., (2016), 102-112.
Hiroshi, Gohda, et al., "In Vivo and in Vitro Metabolism of Cannabidiol Monomethyl Ether and Cannabidiol Dimethyl Ether in the Guinea pig: On the Formation Mechanism of Cannabielsoin-Type Metabolite from Cannabidiol", Chemical and Pharmaceutical vol. 38, No. 6,, (1990), 1697-1701.
Obach, R Scott, "Prediction of Human Clearance of Twenty-Nine Drugs from Hepatic Microsomal Intrinsic Clearance Data: An Examination of In Vitro Half-Life Approach and Nonspecific Binding to Microsomes", Drug Metabolism and Disposition 27(11), [Online]. Retrieved from the Internet: <URL: http://dmd.aspetjournals.org/content/27/11/1350>, (1999), 1350-1359.
Shuso, Takeda, et al., "Cannabidiol-2,6-Dimethyl Ether, a Cannabidiol Derivative, Is a Highly Potent and Selective 15-Lipoxygenase Inhibitor", Drug Metabolism and Disposition, vol. 37, No. 8, (Aug. 2009), 1733-1737.
Watanabe, Kazuhito, et al., "Conversion of cannibidiol to Δ9-tetrahydrocannabinol and related cannabinoids in arti?cial gastric juice, and their pharmacological effects in mice", Forensic Toxicol, vol. 25, (2007), 16-21.

* cited by examiner

*Primary Examiner* — Kahsay Habte
(74) *Attorney, Agent, or Firm* — Schwegman Lundberg & Woessner, P.A.

(57) ABSTRACT

The present disclosure provides biostable cannabinoid compounds according to Formula I:

(I)

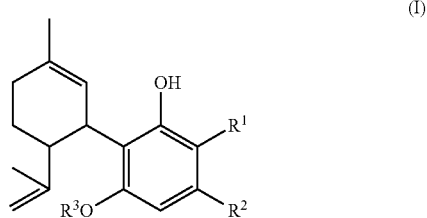

and methods for synthesizing and enhancing the biological concentrations of the compounds, where $R^1$, $R^2$, and $R^3$ are defined as set forth in the disclosure.

21 Claims, No Drawings

BIO-STABLE CANNABINOID COMPOUNDS AND METHODS FOR ENHANCING THEIR PHYSIOLOGICAL CONCENTRATION

PRIORITY

This application claims the benefit of priority to U.S. Provisional Patent Application Ser. No. 62/422,352, filed on Nov. 15, 2016, and which application is incorporated by reference herein in its entirety.

FIELD OF THE INVENTION

The present invention relates to biostable cannabinoid compounds. Specifically, the present invention relates to methods for synthesizing biostable cannabinoid compounds and enhancing the biological concentrations of such compounds.

BACKGROUND OF THE INVENTION

Cannabinoids are terpenophenolic compounds found in *Cannabis sativa*, an annual plant belonging to the Cannabaceae family. The plant contains more than 400 chemicals and approximately 70 cannabinoids. The latter accumulate mainly in the glandular trichomes. The most active of the naturally occurring cannabinoids is tetrahydrocannabinol (THC), which is used for treating a wide range of medical conditions, including glaucoma, AIDS wasting, neuropathic pain, treatment of spasticity associated with multiple sclerosis, fibromyalgia and chemotherapy-induced nausea. THC is also effective in the treatment of allergies, inflammation, infection, epilepsy, depression, migraine, bipolar disorders, anxiety disorder, drug dependency and drug withdrawal syndromes.

Additional active cannabinoids include cannabidiol (CBD), an isomer of THC, which is a potent antioxidant and anti-inflammatory compound known to provide protection against acute and chronic neuro-degeneration. CBD is also used as an antiemetic to control nausea and as an apetite suppressant. In addition, CBD is used for the treatment of epilepsy, schizophrenia and Dravet's syndrome and recent studies suggest therapeutic for treating Alzheimers disease (AD).

Recent studies have shown that CBD converts to THC when exposed to heat or brought in contact with an acid. For instance, oral administration of CBD causes the acid catalyzed cyclization of CBD to THC in gut. The conversion of CBD to THC has limited its use as a therapeutic from the treatment of epilepsy, particularly, in pediatric patients.

The present invention provides methods to prevent the conversion of CBD to THC. Disclosed therefore are methods for synthesizing stable CBD derivatives. The inventive CBD derivatives do not readily convert to THC. Also described are CBD derivatives that are more favorably transported across the blood brain barrier (BBB), permitting an increased therapeutic concentration of CBD or its derivatives in the central nervous system (CNS).

SUMMARY

The present application provides novel CBD derivatives as well as methods for the manufacture of such compounds. In one embodiment, the present invention provides a compound according to Formula I or a pharmaceutically acceptable salt, solvate, or stereoisomer thereof.

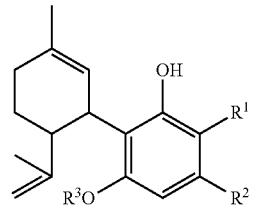

Formula I

For Formula I compounds $R^1$ is —H, —COOR$^4$, or —(CH$_2$)$_n$COOH and substituent $R^2$ is a (C$_1$-C$_{10}$)alkyl or substituted (C$_1$-C$_{10}$)alkyl, such as methyl, ethyl, propyl, butyl, pentyl, hexyl, and heptyl. For some Formula I compounds, $R^3$ is a (C$_1$-C$_{10}$)haloalkyl, an optionally substituted (C$_3$-C$_{10}$)cycloalkyl, an optionally substituted (C$_3$-C$_{10}$)cycloalkyl-(C$_1$-C$_{10}$)alkylene, an optionally substituted —CH$_2$—CH$_2$—[O—CH$_2$—CH$_2$—]$_m$O—CH$_2$—CH$_2$—R$^b$, an optionally substituted —(CHR$^a$)$_q$—NH$_2$, or an optionally substituted —(CHR$^a$)$_q$—NH$^+_3$X$^-$ group.

Substituent R$^a$ is selected from the group consisting of —H, —OH, halogen, (C$_1$-C$_5$) alkyl, and alkoxy, while R$^4$ is —H or (C$_1$-C$_{10}$) alkyl. For Formula I compounds, variable X is a counter ion derived from a pharmaceutically acceptable acid and subscripts n, m and q are each independently integers, for example, 0, 1, 2, 3, 4, 5, 6, 7, 8, 9, or 10.

In one embodiment, substituent $R^1$ in Formula I is —H and substituent $R^2$ is propyl or pentyl. For such Formula I compounds, substituent $R^3$ is chosen from (C$_1$-C$_{10}$) haloalkyl, —CH$_2$—CH$_2$—[O—CH$_2$—CH$_2$—]$_m$O—CH$_2$—CH$_2$—R$^b$, —(CHR$^a$)$_q$—NH$_2$, and —(CHR$^a$)$_q$—NH$^+_3$X$^-$.

When $R^3$ is (C$_1$-C$_{10}$)haloalkyl, suitable haloalkyl groups include without limitation is fluoromethyl, difluoromethyl, trifluoromethyl, fluoroethyl, fluoropropyl, fluorobutyl, fluoro-t-butyl, 1,1,-difluoro-t-butyl, 1,2-difluoro-t-butyl, 1,2,3-trifluoro-t-butyl, and 1,1,2-trifluoro-t-butyl.

In one embodiment $R^3$ is —(CH$_2$)$_2$—[O—CH$_2$—CH$_2$—]$_m$O—(CH$_2$)$_2$—R$^b$, substituent R$^b$ is selected from the group consisting of —OH, —O(C$_1$-C$_5$) alkyl, —(C$_2$-C$_6$) alkene, azide, and —(C$_2$-C$_6$) alkyne, and subscript m is 2 or 3.

According to another embodiment, $R^3$ is terminal alkylammonium salt according to the Formula —(CHR$^a$)$_q$—NH$^+_3$X$^-$ and R$^a$ is —H. Illustrative of such $R^3$ groups without limitation are —(CH$_2$)$_4$—NH$^+_3$X$^-$, —(CH$_2$)$_5$—NH$^+_3$X$^-$, —(CH$_2$)$_6$—NH$^+_3$X$^-$, and —(CH$_2$)$_7$—NH$^+_3$X$^-$.

The claimed invention also provides a method for producing a cannabinoid compound according to Formula IIa or a pharmaceutically acceptable salt, solvate, or stereoisomer thereof, by

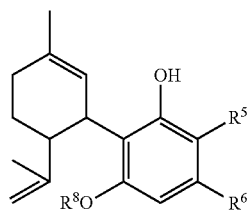

Formula IIa (i) contacting a compound of Formula III

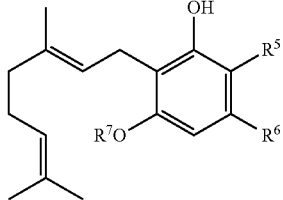

Formula III with a cannabinoid synthase in the presence of a solvent to produce a compound according to Formula II, and then

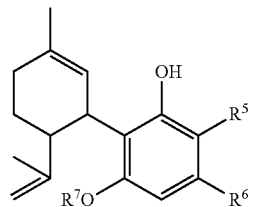

Formula II (ii) contacting the Formula II compound with a suitable Y—$R^8$ group to produce a compound according to Formula IIa. Variable Y in Y—$R^8$ is a leaving group, for example a chloride, bromide, tosylate, mesylate, an alkoxide, maleimide, iodocateamide or —$OBF_3$ group.

For Formula II, IIa, and III compounds, $R^5$ is —H, —$COOR^9$, or —$(CH_2)_n COOH$, and substituent $R^6$ is methyl, ethyl, propyl, butyl, pentyl, hexyl, or heptyl.

According to an embodiment of the method, a Formula II compound where $R^7$ is —H is contacted with a Y—$R^8$ group to provide Formula IIa compounds. Substituent $R^8$ is any group chosen from an optionally substituted ($C_1$-$C_{10}$) alkyl, ($C_1$-$C_{10}$)haloalkyl, optionally substituted ($C_3$-$C_{10}$)aryl, optionally substituted ($C_3$-$C_{10}$)cycloalkyl, optionally substituted ($C_3$-$C_{10}$)aryl-($C_1$-$C_{10}$)alkylene, optionally substituted ($C_3$-$C_{10}$)cycloalkyl-($C_1$-$C_{10}$)alkylene, optionally substituted —$CH_2$—$CH_2$—[O—$CH_2$—$CH_2$—]$_m$O—$CH_2$—$CH_2$—$R^b$, optionally substituted —$(CHR^a)_q$—$NH_2$, and optionally substituted —$(CHR^a)_q$—$NH^+_3 X^-$.

In one embodiment, $R^8$ is ($C_1$-$C_{10}$) alkyl, for example a group chosen from methyl, ethyl, propyl, butyl, t-butyl, pentyl, hexyl, or heptyl.

According to another embodiment, $R^8$ is —$(CHR^a)_q$—$NH_2$, or —$(CHR^a)_q$—$NH^+_3 X^-$, and X is a counter ion derived from a pharmaceutically acceptable acid. For such compounds, $R^a$ is selected from the group consisting of —H, —OH, halogen, ($C_1$-$C_5$) alkyl, and alkoxy and subscript q is 4, 5, 6, or 7.

According to yet another embodiment, $R^8$ is —$(CH_2)_2$—[O—$CH_2$—$CH_2$—]$_m$O—$(CH_2)_2$—OH and m is 2 or 3.

For some Formula IIa compounds, $R^5$ is —$COOR^9$ and $R^9$ is —H or ($C_1$-$C_{10}$) alkyl. In one embodiment, $R^9$ is —H. For Formula IIa compounds, subscripts n, m and q are each independently integers chosen from 0, 1, 2, 3, 4, 5, 6, 7, 8, 9, or 10.

In one embodiment, for inventive compounds according to Formula IIa, $R^5$ is —H and $R^6$ is propyl or pentyl. According to another embodiment, the Formula II compound produced using the inventive method is de-carboxylated prior to its use as a therapeutic agent. De-carboxylation is accomplished by contacting a solution of the Formula II compound to heat or by exposing a solution of the Formula II compound to UV-light.

In one embodiment of the inventive method, the cannabinoid synthase is cannabidiolic acid synthase (CBDA synthase) and the step of contacting the Formula III compound with CBDA synthase is performed in a solution of CBDA synthase.

In yet another embodiment, the disclosure provides a method for enhancing the physiological concentration of a Formula IVa compound in a human subject.

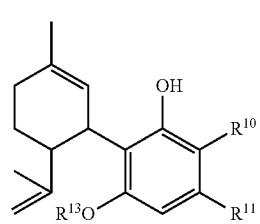

Formula IVa

According to the inventive method, the Formula IVa compound is obtained by contacting a Formula IV compound where $R^{12}$ is —H and $R^{10}$ and $R^{11}$ are as defined below, with a suitable Z—$R^{13}$ group. The biological concentration of the Formula IVa compound thus obtained, when measured as the area under a curve of the plasma concentration against time, is in the range from about 2 ng/mL to 25 ng/mL per milligram of the Formula IVa compound administered to the subject.

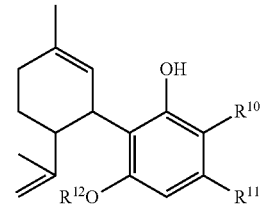

Formula IV

For Formula IV and IVa compounds, substituent $R^{10}$ is —H, —$COOR^{14}$, or —$(CH_2)_n COOH$ and substituent $R^{11}$ is methyl, ethyl, propyl, butyl, pentyl, hexyl, or heptyl.

In one embodiment, substituent $R^{13}$ in Formula IVa is an optionally substituted ($C_1$-$C_{10}$) alkyl, ($C_1$-$C_{10}$)haloalkyl, an optionally substituted ($C_3$-$C_{10}$)aryl, an optionally substituted ($C_3$-$C_{10}$)cycloalkyl, an optionally substituted ($C_3$-$C_{10}$) aryl-($C_1$-$C_{10}$)alkylene, an optionally substituted ($C_3$-$C_{10}$) cycloalkyl-($C_1$-$C_{10}$)alkylene, an optionally substituted —$CH_2$—$CH_2$—[O—$CH_2$—$CH_2$—]$_m$O—$CH_2$—$CH_2$—$R^b$, an optionally substituted —$(CHR^a)_q$—$NH_2$, or an optionally substituted —$(CHR^a)_q$—$NH^+_3 X^-$ group and $R^a$ is —H, —OH, halogen, ($C_1$-$C_5$) alkyl, or alkoxy.

In one embodiment, $R^{13}$ is —$(CHR^a)_q$—$NH^+_3 X^-$ group and X is a counter ion derived from a pharmaceutically acceptable acid.

For certain Formula IV and IVa compounds, $R^{10}$ is —$COOR^{14}$, and $R^{14}$ is —H or ($C_1$-$C_{10}$) alkyl. Variable Z in Z—$R^{13}$ is a leaving group, for example a chloride, bromide, tosylate, mesylate, an alkoxide, maleimide, iodocateamide or —$OBF_3$ group, while subscripts n, m and q are each independently 0, 1, 2, 3, 4, 5, 6, 7, 8, 9, or 10.

In yet another aspect, the invention provides a method for treating a neurological disorder in a subject by administering a therapeutically effective amount of a Formula V compound to the subject in need of treatment.

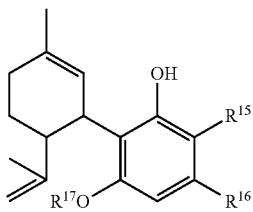

Formula V

For Formula V compounds, $R^{15}$ is —H, —COOR$^{18}$, or —(CH$_2$)$_n$COOH, substituent $R^{16}$ is selected from the group consisting of methyl, ethyl, propyl, butyl, pentyl, hexyl, and heptyl and substituent $R^{17}$ is an optionally substituted (C$_1$-C$_{10}$) alkyl, (C$_1$-C$_{10}$) haloalkyl, optionally substituted (C$_3$-C$_{10}$)aryl, optionally substituted (C$_3$-C$_{10}$)cycloalkyl, optionally substituted (C$_3$-C$_{10}$)aryl-(C$_1$-C$_{10}$)alkylene, optionally substituted (C$_3$-C$_{10}$)cycloalkyl-(C$_1$-C$_{10}$)alkylene, optionally substituted —CH$_2$CH$_2$—[O—CH$_2$—CH$_2$—]$_m$O—CH$_2$—CH$_2$—R$^b$, optionally substituted —(CHR$^a$)$_q$—NH$_2$, and optionally substituted —(CHR$^a$)$_q$—NH$^+_3$X$^-$.

When $R^{17}$ is —(CHR$^a$)$_q$—NH$_2$, or —(CHR$^a$)$_q$—NH$^+_3$X$^-$, $R^a$ is selected from the group consisting of —H, —OH, halogen, (C$_1$-C$_5$) alkyl, and alkoxy and X is a counter ion derived from a pharmaceutically acceptable acid.

For Formula V compounds, subscripts n, m and q are each independently 0, 1, 2, 3, 4, 5, 6, 7, 8, 9, or 10.

DETAILED DESCRIPTION

Definitions

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The term "alkyl" refers to a straight or branched chain, saturated hydrocarbon having the indicated number of carbon atoms. For example, (C$_1$-C$_{10}$)alkyl is meant to include but is not limited to methyl, ethyl, propyl, isopropyl, butyl, sec-butyl, tert-butyl, pentyl, isopentyl, neopentyl, hexyl, isohexyl, and neohexyl, etc. An alkyl group can be unsubstituted or optionally substituted with one or more substituents as described herein below.

The term "alkenyl" or "alkene" refers to a straight or branched chain unsaturated hydrocarbon having the indicated number of carbon atoms and at least one double bond. Examples of a (C$_2$-C$_{10}$)alkenyl group include, but are not limited to, ethene, propene, 1-butene, 2-butene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term "alkynyl" refers to a straight or branched chain unsaturated hydrocarbon having the indicated number of carbon atoms and at least one triple bond. Examples of a (C$_2$-C$_{10}$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "haloalkyl" refers to an alkyl group having the indicated number of carbon atoms wherein one or more of the alkyl group's hydrogen atoms is replaced with a halogen. Examples of haloalkyl groups include, but are not limited to, FCH$_2$—, HCF$_2$—, CF$_3$—, FCH$_2$—CH$_2$—, FCH$_2$—CH$_2$—CH$_2$, —C(CH$_3$)$_2$(FCH$_2$), —C(FCH$_2$)$_2$(CH$_3$), —C(FCH$_2$)$_3$, and —C(FCH$_2$)$_2$(CHF$_2$).

The term "alkoxy" refers to an —O-alkyl group having the indicated number of carbon atoms. For example, a (C$_1$-C$_6$)alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aryl" refers to a 3- to 14-member monocyclic, bicyclic, tricyclic, or polycyclic aromatic hydrocarbon ring system. Examples of an aryl group include naphthyl, pyrenyl, and anthracyl. An aryl group can be unsubstituted or optionally substituted with one or more substituents as described herein below.

The terms "alkylene," "cycloalkylene," "alkenylene," "alkynylene." "arylene," and "heteroarylene," alone or as part of another substituent, means a divalent radical derived from an alkyl, cycloalkyl, alkenyl, alkynyl, aryl, or heteroaryl group, respectively, as exemplified by —CH$_2$CH$_2$CH$_2$CH$_2$—. For alkylene, alkenylene, or aryl linking groups, no orientation of the linking group is implied.

The term "halogen" and "halo" refers to —F, —Cl, —Br or —I.

The term "heteroatom" is meant to include oxygen (O), nitrogen (N), and sulfur (S).

A "hydroxyl" or "hydroxy" refers to an —OH group.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "cycloalkyl" or "carbocycle" refer to monocyclic, bicyclic, tricyclic, or polycyclic, 3- to 14-membered ring systems, which are either saturated, unsaturated or aromatic. The heterocycle may be attached via any heteroatom or carbon atom. Cycloalkyl include aryls and hetroaryls as defined above. Representative examples of cycloalky include, but are not limited to, cycloethyl, cyclopropyl, cycloisopropyl, cyclobutyl, cyclopentyl, cyclohexyl, cyclopropene, cyclobutene, cyclopentene, cyclohexene, phenyl, naphthyl, anthracyl, benzofuranyl, and benzothiophenyl. A cycloalkyl group can be unsubstituted or optionally substituted with one or more substituents as described herein below.

The term "amine or amino" refers to an —NR$_c$R$_d$ group wherein R$_c$ and R$_d$ each independently refer to a hydrogen, (C$_1$-C$_8$)alkyl, aryl, heteroaryl, heterocycloalkyl, (C$_1$-C$_8$)haloalkyl, and (C$_1$-C$_6$)hydroxyalkyl group.

The term "alkylaryl" refers to $C_1$-$C_8$ alkyl group in which at least one hydrogen atom of the $C_1$-$C_8$ alkyl chain is replaced by an aryl atom, which may be optionally substituted with one or more substituents as described herein below. Examples of alkylaryl groups include, but are not limited to, methylphenyl, ethylnaphthyl, propylphenyl, and butylphenyl groups.

"Arylalkylene" refers to a divalent alkylene wherein one or more hydrogen atoms in the $C_1$-$C_{10}$ alkylene group is replaced by a $(C_3$-$C_{14})$aryl group. Examples of $(C_3$-$C_{14})$aryl-$(C_1$-$C_{10})$alkylene groups include without limitation 1-phenylbutylene, phenyl-2-butylene, 1-phenyl-2-methylpropylene, phenylmethylene, phenylpropylene, and naphthylethylene.

The terms "carboxyl" and "carboxylate" include such moieties as may be represented by the general formula:

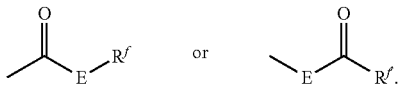

E in the formula is a bond or O and $R^f$ individually is H, alkyl, alkenyl, aryl, or a pharmaceutically acceptable salt. Where E is O, and $R^f$ is as defined above, the moiety is referred to herein as a carboxyl group, and particularly when $R^f$ is a hydrogen, the formula represents a "carboxylic acid". In general, where the expressly shown oxygen is replaced by sulfur, the formula represents a "thiocarbonyl" group.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

In the context of the present invention the term "derivative" refers to a compound that is structurally related to naturally occurring cannabinoids, but whose chemical and biological properties may differ from naturally occurring cannabinoids. In the present context, derivative or derivatives refer compounds that may not exhibit one or more unwanted side effects of a naturally occurring cannabinoid. Derivative also refers to a compound that is derived from a naturally occurring cannabinoid by chemical, biological or a semi-synthetic transformation of the naturally occurring cannabinoid.

Accordingly, in one of its embodiments the present invention provides a derivative of a cannabinoid compound that has improved biostability and increased bioavailability than a naturally occurring cannabinoid compound. Because of its increased biostability and bioavailability, the biological concentration of the inventive cannabinoid derivative is greater than the biological concentration of a naturally occurring cannabinoid compound.

In one embodiment, a cannabinoid derivative of the invention is a compound according to Formula I.

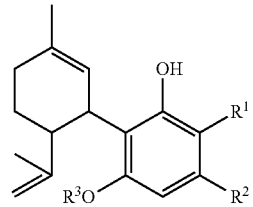

Formula I

For Formula I compounds, $R^1$ is —H, —COOR$^4$, or —(CH$_2$)$_n$COOH. In one embodiment, $R^1$ is —H and $R^2$ is a $(C_1$-$C_{10})$ alkyl group. Exemplary alkyl groups include without limitation methyl, ethyl, propyl, butyl, pentyl, hexyl, and heptyl.

For some Formula I compounds $R^1$ is —H and $R^2$ is propyl, butyl, or pentyl. Thus, the disclosure provides Formula I compounds where $R^1$ is —H and $R^2$ is propyl. Also encompassed are Formula I compounds where $R^1$ is —H and $R^2$ is pentyl.

According to another embodiment, $R^1$ is —COOR$^4$ and $R^2$ is propyl or pentyl. For such compounds $R^4$ can be —H or an alkyl group. In one embodiment $R^4$ is —H. Thus, for certain Formula I compounds according to the invention, $R^1$ is —COOH and $R^2$ is propyl. For other Formula I compounds $R^1$ is —COOH and $R^2$ is pentyl.

In one embodiment, for Formula I compounds of the invention, $R^1$ is —(CH$_2$)$_n$COOH, substituent $R^2$ is methyl, ethyl, propyl, butyl, or pentyl, and the subscript "n" is 1, 2, 3, or 4. According to another embodiment, $R^1$ is —(CH$_2$)$_n$COOH, $R^2$ is propyl, or pentyl, and the subscript "n" is 1, 2, 3, or 4.

For some Formula I, compounds when $R^1$ is —(CH$_2$)$_n$COOH, "n" is 1 or 2, and $R^2$ is propyl. For other Formula I compounds $R^1$ is —(CH$_2$)$_n$COOH, "n" is 1 or 2, and $R^2$ is pentyl. In one embodiment, $R^1$ is —(CH$_2$)COOH and $R^1$ is propyl or pentyl.

For certain Formula I compounds, $R^3$ is a $(C_1$-$C_{10})$haloalkyl. In one embodiment, $R^1$ is —COOH, $R^2$ is propyl or pentyl and $R^3$ is —CF$_3$.

According to another embodiment, the Formula I compound where $R^1$ is —COOH, $R^2$ is propyl or pentyl and $R^3$ is —CF$_3$, is de-carboxylated (removal of CO$_2$) as further described below. Such de-carboxylation can be performed, prior to the use of the Formula I compound as a therapeutic agent.

For some other Formula I compounds $R^1$ is —COOH or —H, $R^2$ is propyl or pentyl and $R^3$ is fluoro-t-butyl, 1,1,-difluoro-t-butyl, 1,2-difluoro-t-butyl, 1,2,3-trifluoro-t-butyl, and 1,1,2-trifluoro-t-butyl.

In one embodiment, $R^3$ in Formula I is a polyethylene glycol (PEG) group, for example, a —(CH$_2$)$_2$—[O—CH$_2$—CH$_2$—]$_m$O—(CH$_2$)$_2$—R$^b$ group. For such compounds, R$^b$ is selected from the group consisting of —OH, —O(C$_1$-C$_5$)

alkyl, —($C_2$-$C_6$) alkene, and —($C_2$-$C_6$) alkyne, and subscript "m" is any integer, such as 1, 2, 3, 4, 5, 6, or 7.

In one embodiment, $R^1$ is —COOH or —H, $R^2$ is propyl or pentyl and $R^3$ is a PEG group, for example, a —($CH_2$)$_2$—[O—$CH_2$—$CH_2$—]$_2$O—($CH_2$)$_2$—OH or a —($CH_2$)$_2$—[O—$CH_2$—$CH_2$—]$_3$O—($CH_2$)$_2$—OH group.

In one embodiment, $R^1$ is —COOH, $R^2$ is propyl and $R^3$ is a group chosen from —($CH_2$)$_2$—[O—$CH_2$—$CH_2$—]$_2$O—($CH_2$)$_2$—OH, —($CH_2$)$_2$—[O—$CH_2$—$CH_2$—]$_2$O—($CH_2$)$_2$—$N_3$, —($CH_2$)$_2$—[O—$CH_2$—$CH_2$—]$_2$O—($CH_2$)$_2$—C≡CH group.

In another embodiment, $R^1$ is —COOH, $R^2$ is pentyl and $R^3$ is a —($CH_2$)$_2$—[O—$CH_2$—$CH_2$—]$_2$O—($CH_2$)$_2$—OH group. Such Formula I compounds can be de-carboxylated prior to their administration to a subject.

Alternatively, under certain circumstances, the Formula I compound in which $R^1$ is —COOH or —H, $R^2$ is propyl or pentyl and $R^3$ is —H is de-carboxylated prior to contacting such a compound with an appropriate agent to obtain a compound of the invention where $R^1$ is —H, $R^2$ is propyl or pentyl and $R^3$ is a —($CH_2$)$_2$—[O—$CH_2$—$CH_2$—]$_m$O—($CH_2$)$_2$—OH group.

For some Formula I compounds, $R^3$ is —(CHR$^a$)$_q$—NH$^+_3$X$^-$ or —(CHR$^a$)$_q$—NH$_2$, and R$^a$ is a group selected from —H, —OH, halogen, ($C_1$-$C_5$) alkyl, and alkoxy. In one embodiment, $R^3$ is —(CH$^2$)$_q$—NH$^+_3$X$^-$, subscript "q" is 1, 2, 3, 4, or 5 and X$^-$ is chloride, formic, acetic, propionic, lactate, tartarate, succinate, hemisuccinate, glycolic, gluconic, phosphate, or sulfate.

Formula I compounds can be de-carboxylated prior to use by contacting the Formula I compound with heat. According to another embodiment, decarboxylation takes place by contacting a solution of a Formula I compound to heat or exposing a solution of the Formula I compound to UV-light. Alternatively, decarboxylation takes place by contacting a solution of a Formula I compound with a weak base such as sodium bicarbonate.

Illustrative Formula I compounds where $R^1$ is —COOH are those structurally represented below in Table 1.

TABLE 1

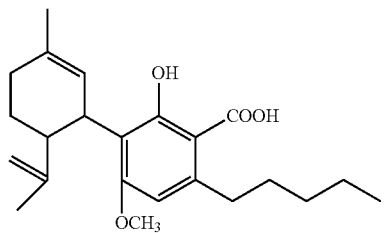 [SMILES: C=C(C)C1CCC(C)=CC1c1c(OC)cc(CCCCC)c(C(=O)O)c1O]

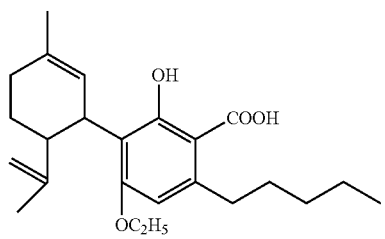 [SMILES: C=C(C)C1CCC(C)=CC1c1c(OCC)cc(CCCCC)c(C(=O)O)c1O]

TABLE 1-continued

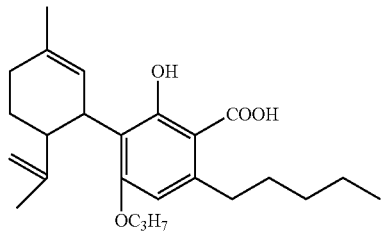

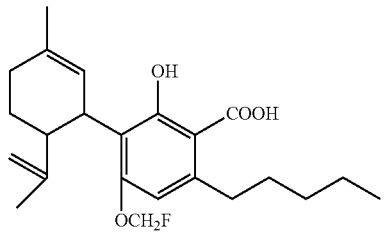

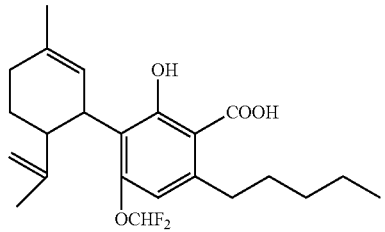

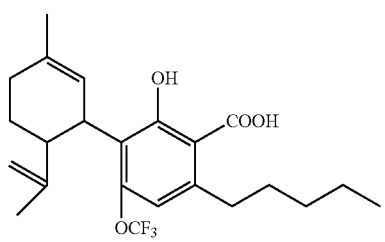

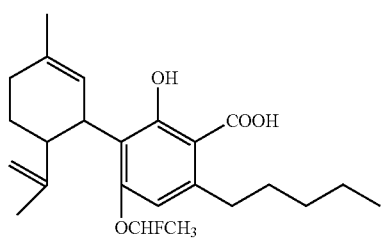

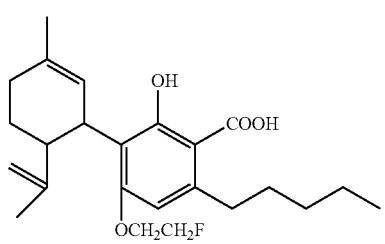

TABLE 1-continued
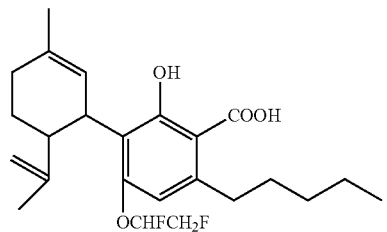
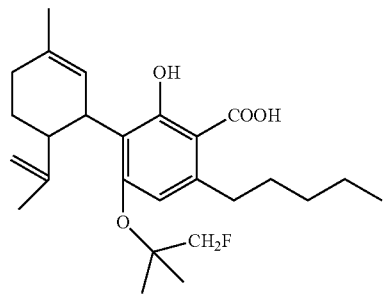
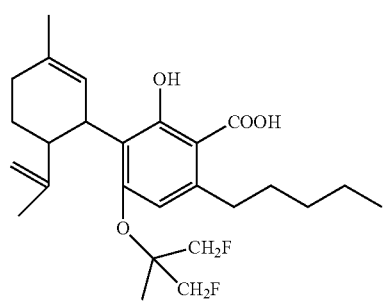
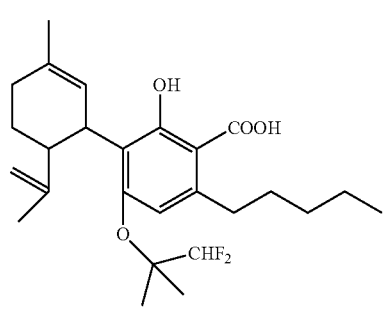 [SMILES: C=C(C)C1CCC(C)=CC1c1c(OC(C)(C)C(F)F)cc(CCCCC)c(C(=O)O)c1O]
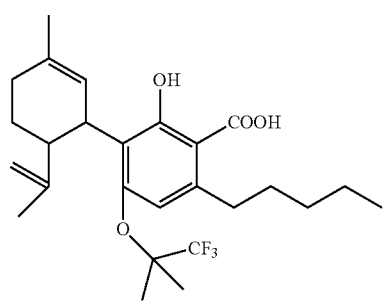 [SMILES: C=C(C)C1CCC(C)=CC1c1c(OC(C)(C)C(F)(F)F)cc(CCCCC)c(C(=O)O)c1O]
TABLE 1-continued
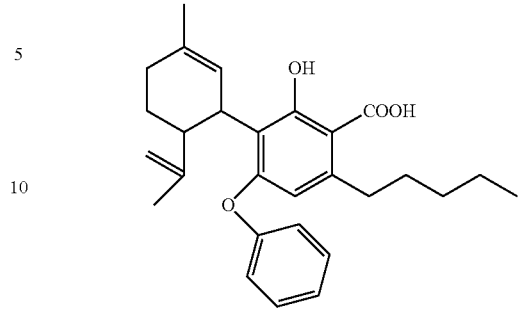
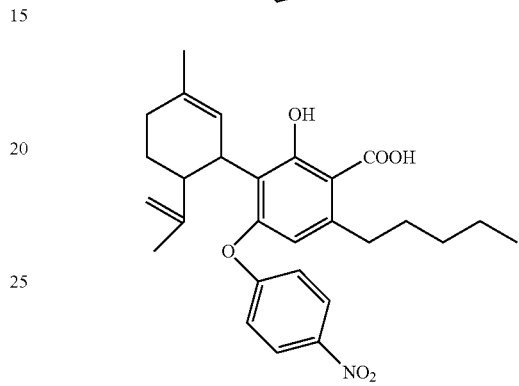
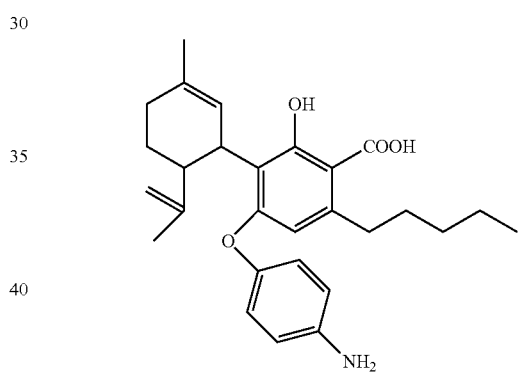
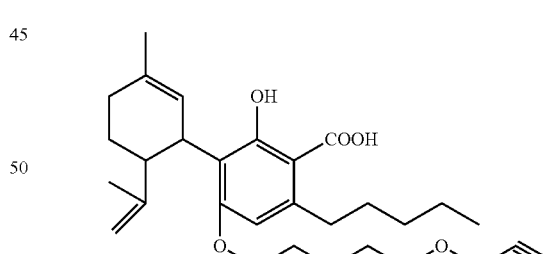
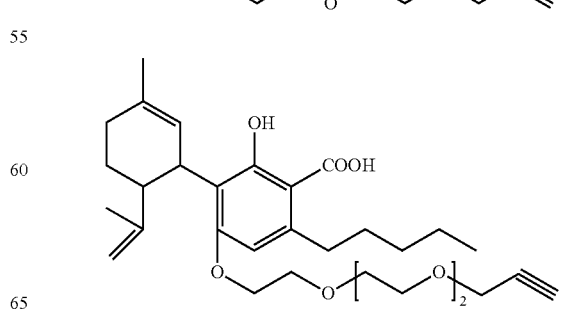

TABLE 1-continued
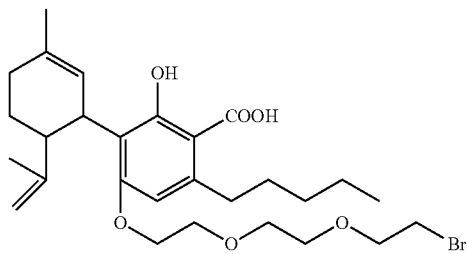 [SMILES: C=C(C)C1CCC(C)=CC1c1c(OCCOCCOCCBr)cc(CCCCC)c(C(=O)O)c1O]
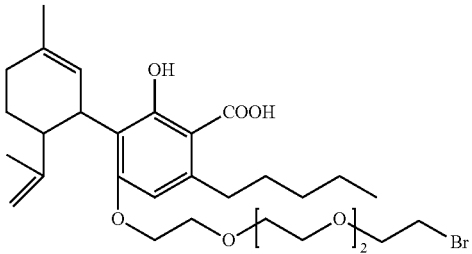
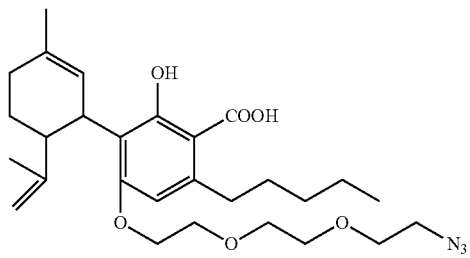 [SMILES: C=C(C)C1CCC(C)=CC1c1c(OCCOCCOCCN=[N+]=[N-])cc(CCCCC)c(C(=O)O)c1O]
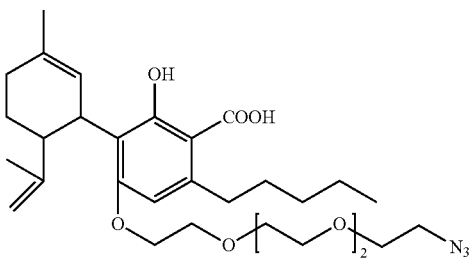
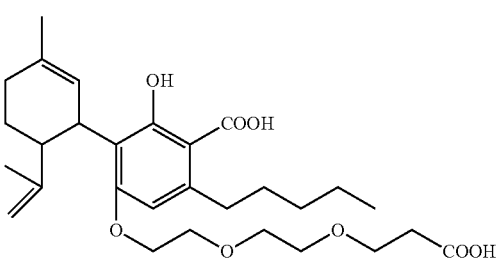 [SMILES: C=C(C)C1CCC(C)=CC1c1c(OCCOCCOCCC(=O)O)cc(CCCCC)c(C(=O)O)c1O]
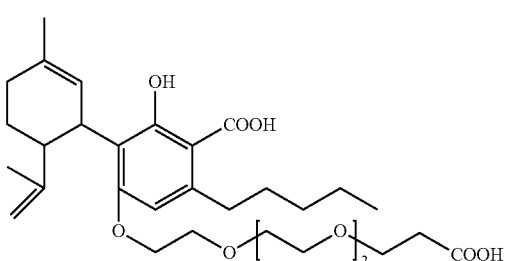
TABLE 1-continued
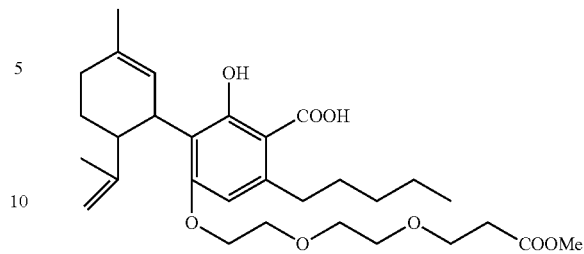
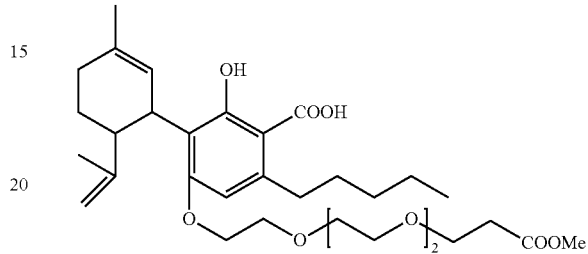
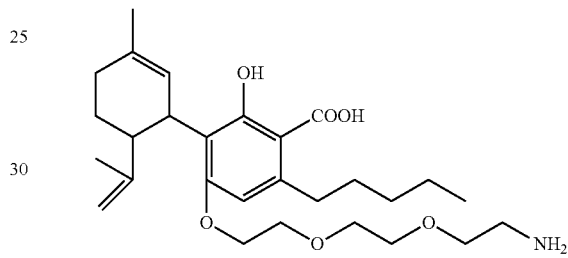
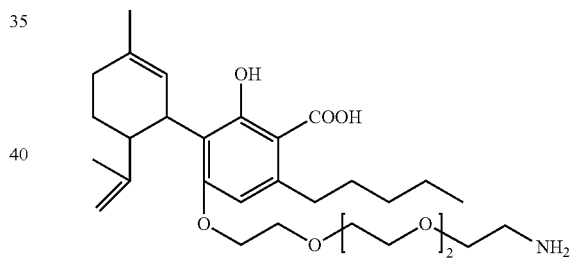
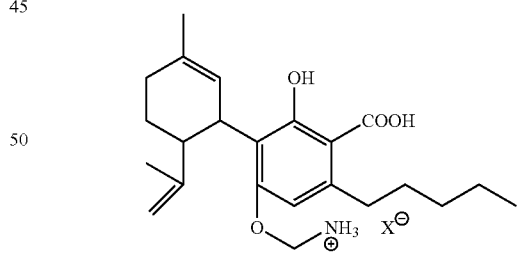
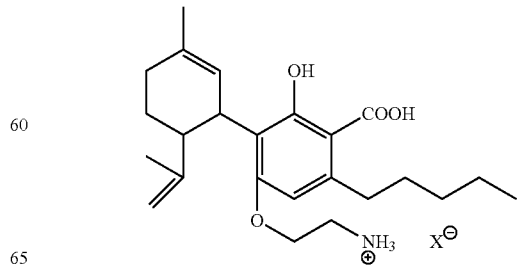

TABLE 1-continued
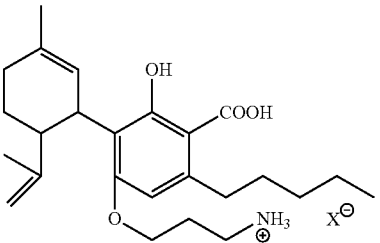
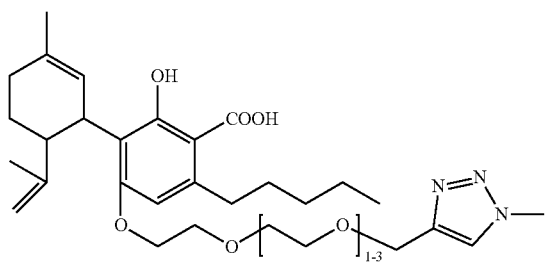
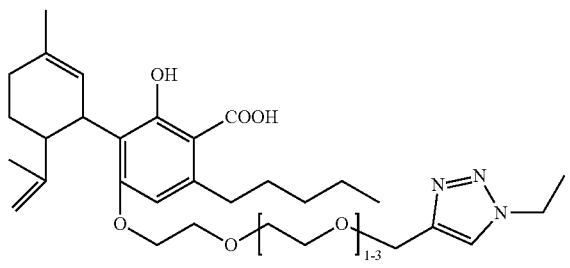
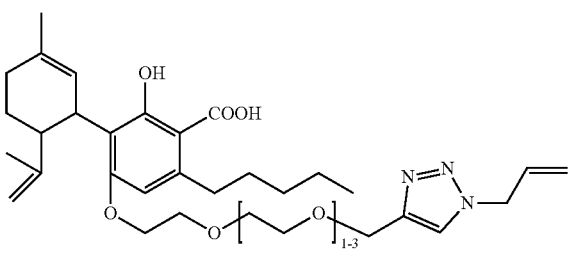
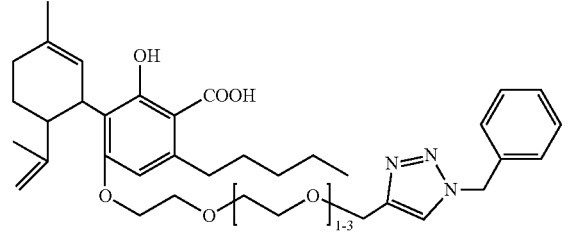
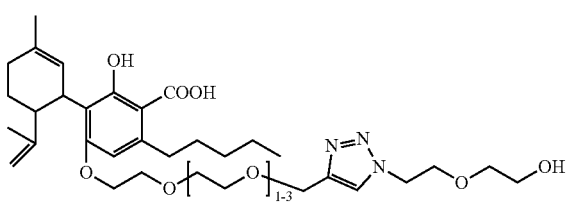
TABLE 1-continued
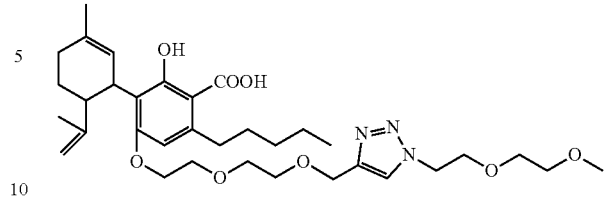
As described in this disclosure, compounds of Formula I can be de-carboxylated prior to their use as therapeutic agents. Illustrative Formula I compounds where $R^1$ is —H are those structurally represented below in Table 2.
TABLE 2
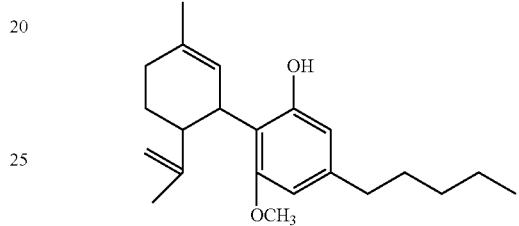
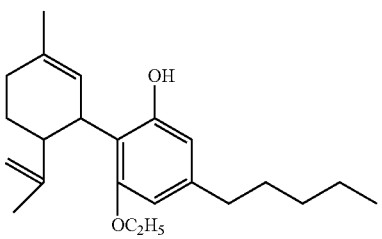 [SMILES: C=C(C)C1CCC(C)=CC1c1c(O)cc(CCCCC)cc1OCC]
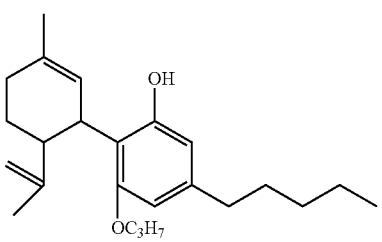
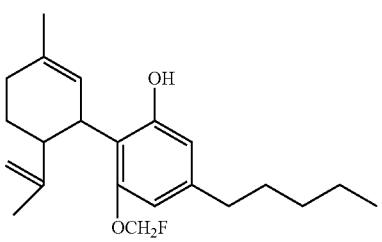
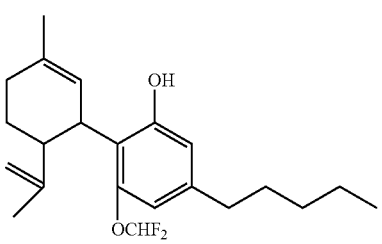

TABLE 2-continued
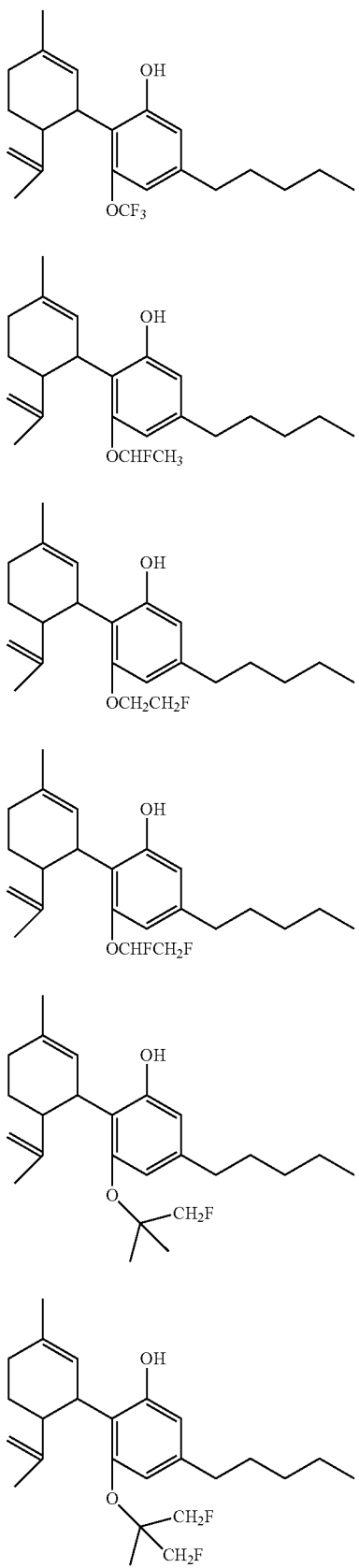
TABLE 2-continued
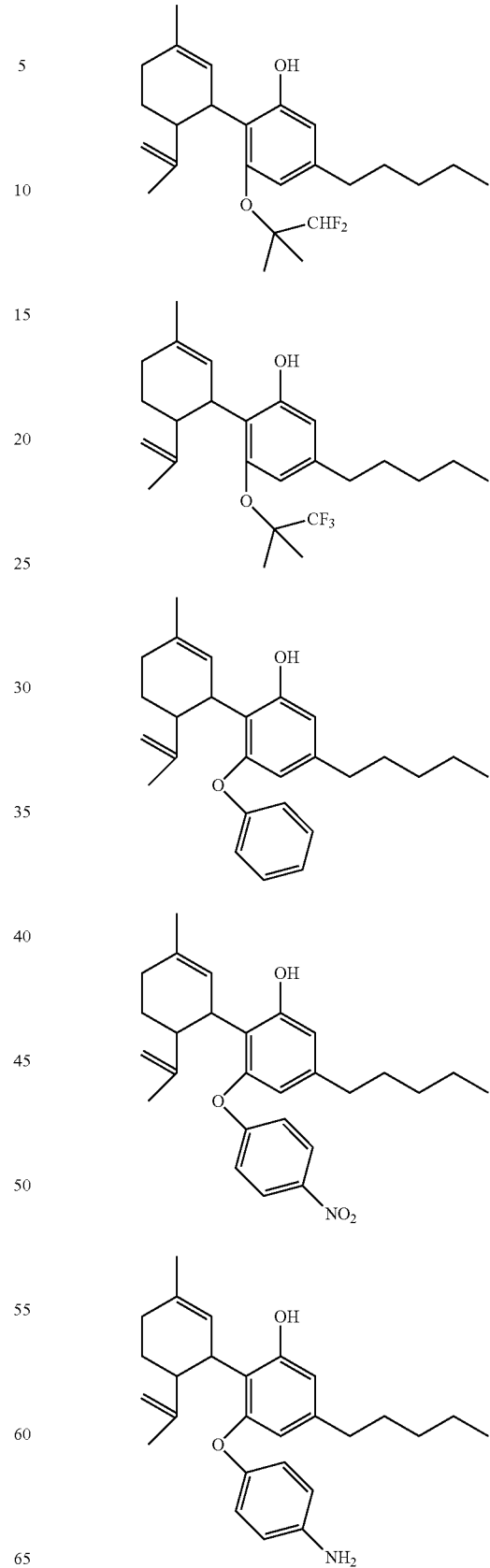

TABLE 2-continued
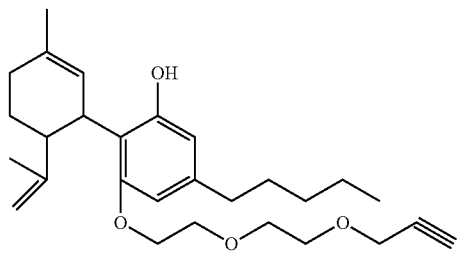 [SMILES: C#CCOCCOCCOc1cc(CCCCC)cc(O)c1C1C=C(C)CCC1C(=C)C]
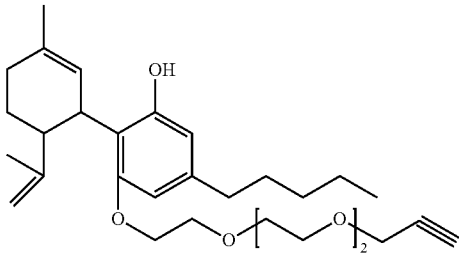
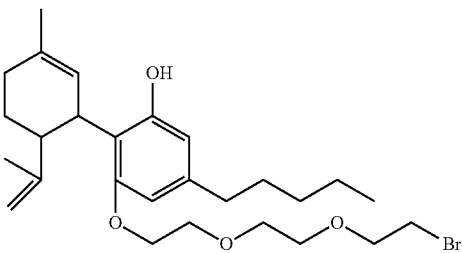 [SMILES: C=C(C)C1CCC(C)=CC1c1c(O)cc(CCCCC)cc1OCCOCCOCCBr]
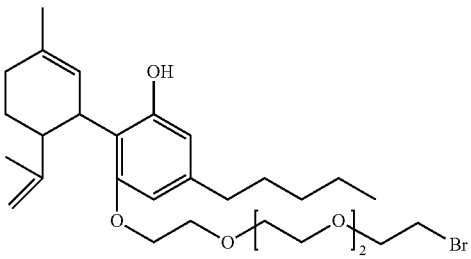
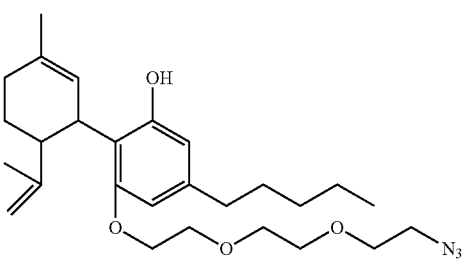 [SMILES: C=C(C)C1CCC(C)=CC1c1c(O)cc(CCCCC)cc1OCCOCCOCCN=[N+]=[N-]]
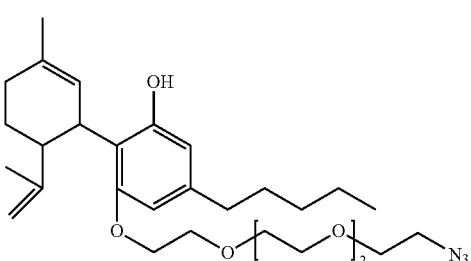
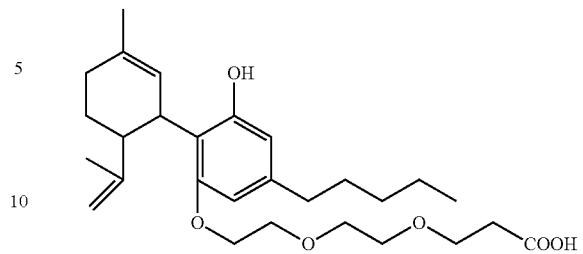
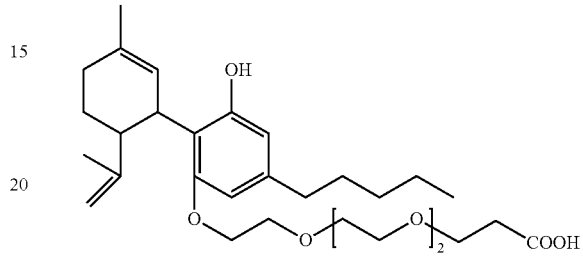
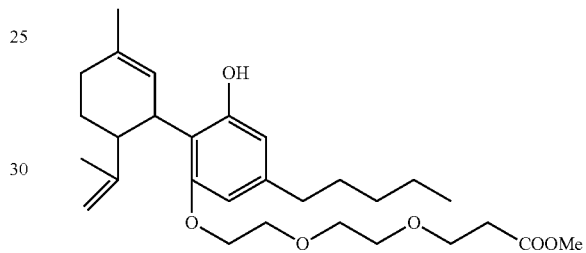
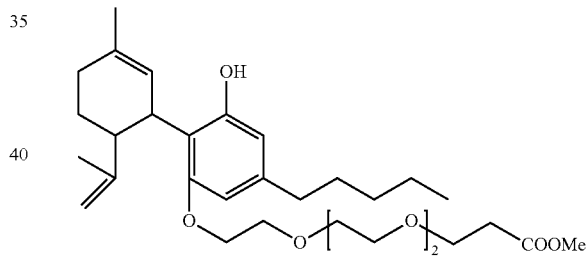
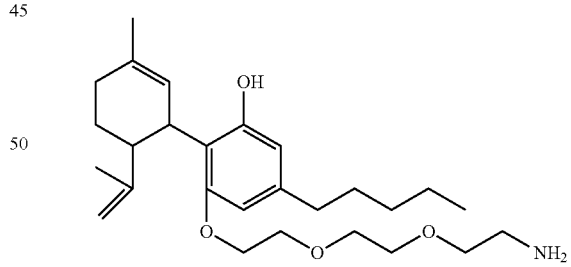
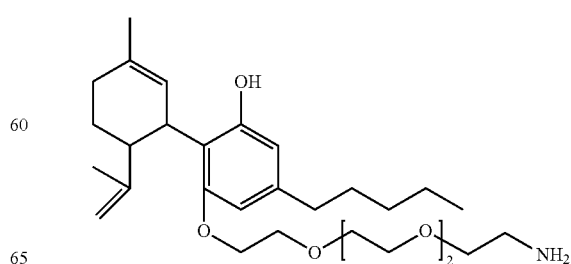

TABLE 2-continued

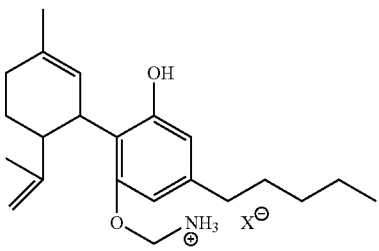
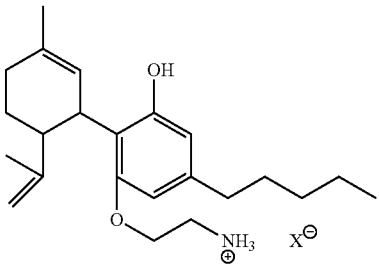
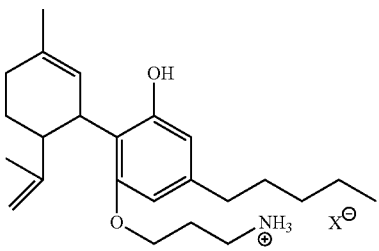
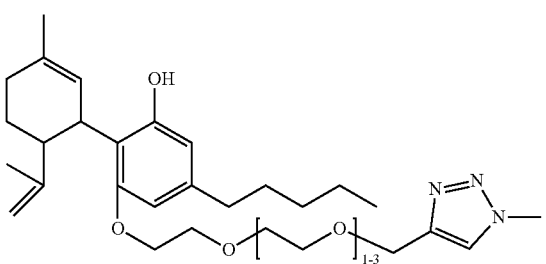
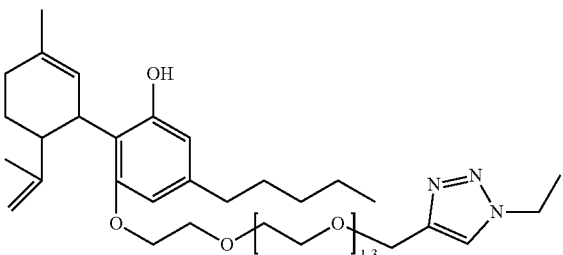
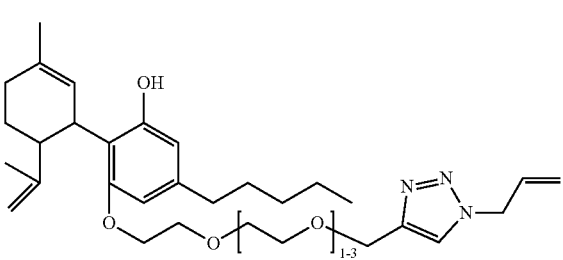

TABLE 2-continued

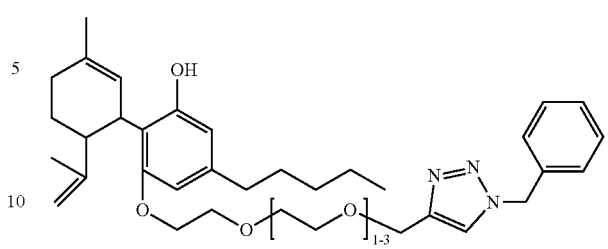
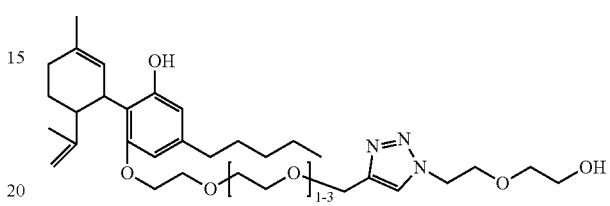
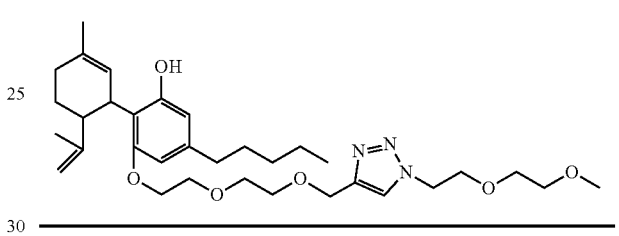

Also described is a method for synthesizing a compound of the invention as well as methods for using the inventive compounds to treat neurological conditions. Accordingly, in one of its aspects, the application provides a method for producing a compound according to Formula IIa or a pharmaceutically acceptable salt, solvate, or stereoisomer thereof.

Formula IIa

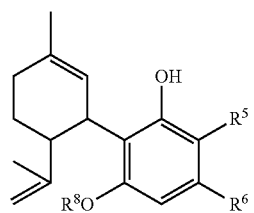

According to this method, a Formula IIa compound is obtained by contacting a compound of Formula III Formula III

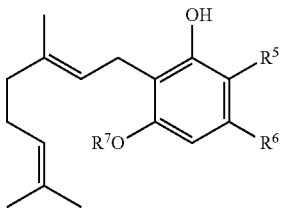

with a cannabinoid synthase in the presence of a solvent to produce a compound according to Formula II Formula II

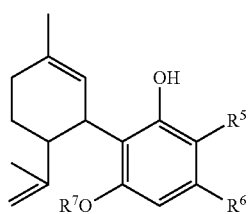

Further contact of the Formula II compound with a suitable Y—R⁸ group produces the Formula IIa compound.

For Formula II, IIa and III compounds, $R^5$ is a group chosen from —H, —COOR⁹, or —(CH₂)$_n$COOH, while $R^6$ is an alkyl group chosen from methyl, ethyl, propyl, butyl, pentyl, hexyl, or heptyl.

In one embodiment, $R^5$ is —H, and $R^6$ is propyl, or pentyl. According to another embodiment, $R^5$ is —COOR⁹, and $R^6$ is an alkyl group chosen from methyl, ethyl, propyl, butyl, pentyl, hexyl, or heptyl.

When $R^5$ is —COOR⁹, $R^9$ can be —H or alkyl, for example, an alkyl group chosen from methyl, ethyl, propyl, butyl, pentyl, hexyl, or heptyl.

As disclosed above, contacting a Y—R⁸ group with a Formula II compound under suitable conditions produces a Formula IIa compound. The group Y—R⁸ is a reagent that can be obtained commercially or may be synthesized chemically or biochemically using protocols known in the chemical or biochemical art.

In one embodiment, a solution of a Formula II compound where $R^7$ is —H is contacted with a Y—R⁸ group or a solution of a Y—R⁸ group. The synthesis of the Formula IIa compound can be facilitated by the addition of a base, and acid or a suitable catalyst. For example, in one aspect of this method, a base is added to a solution of a Formula II compound prior to contact of a solution of a Formula II compound with a Y—R⁸ group.

Scheme 1 illustrates one synthetic protocol for making a Formula IIa compound. Specifically, Scheme 1 illustrates methodologies for conjugating various alkyl and haloalkyl groups to a Formula II compound. The synthesis of such Formula IIa compounds proceeds by contacting a solution of a Formula II compound where $R^3$ is —H with a base, followed by contacting of the resulting oxygen anion with the desired Y—R⁸ group, for example, an alkyl-Y or haloalkyl-Y group.

Scheme 1

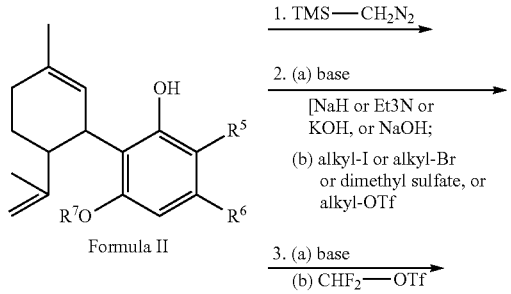

For Y—R⁸, variable "Y" is a suitable leaving, while $R^8$ is alkyl or haloalkyl. In one embodiment, the Formula II compound is contacted with an alkyl halide or alkyl triflate to produce a Formula IIa compound.

According to another embodiment, $R^8$ of group Y—R⁸ is a haloalkyl halide, such as a haloalkyl-bromide or haloalkyl-chloride. Exemplary haloalkyl-halides include fluoromethyl bromide, difluoromethyl bromide, trifluoromethyl bromide, fluoroethyl bromide, fluoropropyl bromide, fluorobutyl bromide, fluoro-t-butyl bromide, 1,1-difluoro-t-butyl bromide, 1,2-difluoro-t-butyl bromide, 1,2,3-trifluoro-t-butyl bromide, and 1,1,2-trifluoro-t-butyl bromide.

Other exemplary haloalkyl-halides include fluoromethyl chloride, difluoromethyl chloride, trifluoromethyl chloride, fluoroethyl chloride, fluoropropyl chloride, fluorobutyl chloride, fluoro-t-butyl chloride, 1,1-difluoro-t-butyl chloride, 1,2-difluoro-t-butyl chloride, 1,2,3-trifluoro-t-butyl chloride, and 1,1,2-trifluoro-t-butyl chloride.

According to one embodiment, when $R^8$ is alkyl or haloalkyl, and the leaving group "Y" is a triflate, a mesylate, a boron trifluoride ether, a maleimide, trichlorotriazine (TCT), tosylate, or an iodocateamide. Exemplary of such Y—R⁸ groups are R⁸—OTf, R⁸—OMs, or R⁸—OTs.

Methyl ethers of Formula II compounds can be synthesized by contacting an anhydrous THF solution of CBD or CBDA with a THF solution of diazomethane.

Also encompassed within the scope of this disclosure is a method for synthesizing the allyl ether of a Formula II compound by contacting Formula II compound where $R^7$ is —H, with a base such as sodium hydride and reacting the alkoxide anion thus formed with a slight excess of allyl bromide.

Synthesis of aryl ethers, such as benzyl or 4-nitrobenzyl ethers is accomplished by contacting a Formula II compound where $R^7$ is —H with a base and then contacting the resultant alkoxide ion with benzyl bromide, 4-aminobenzyl bromide, or 4-nitrobenzyl bromide to provide a compound according to Formula IIa.

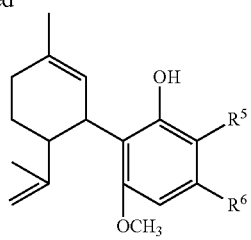

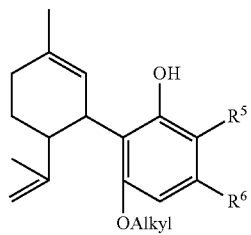

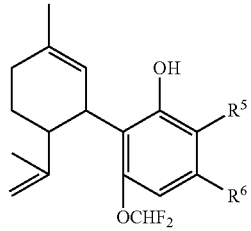

Scheme 2 illustrates alternative synthetic protocols for the manufacture of benzyl ethers of a Formula II compound. In one embodiment, the benzyl ether is synthesized by contacting the Formula II compound with benzyloxy trichloroacetimidate under mild acidic conditions.

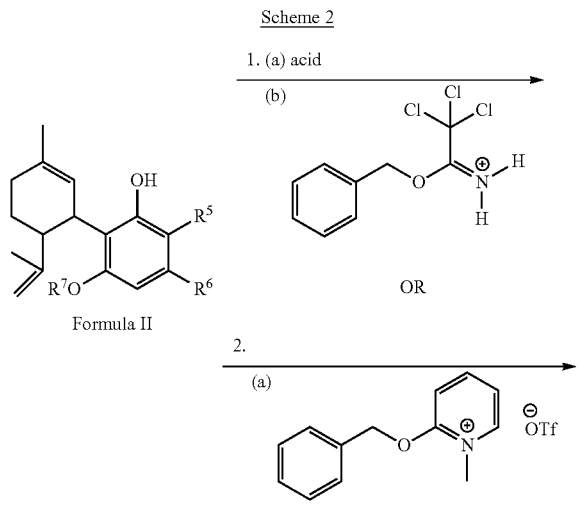

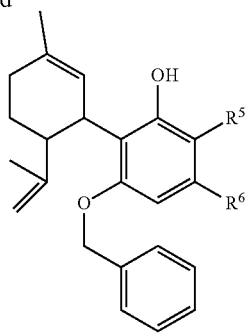

According to an alternate embodiment, benzyl ethers of a Formula II compound are obtained under neutral conditions by contacting the Formula II compound with a toluene or THF solution of 2-benzyloxy-N-methylpyridinium triflate.

Schemes 3, 4 and 5 illustrate Formula IIa compounds where $R^8$ is polyethylene glycol (PEG) or a derivative of PEG. Scheme 3 illustrates the manufacture of Formula IIa compounds with a terminal alkyne group. Such Formula IIa compounds can be further modified by routine chemical methods known in the synthetic art.

For example, the terminal alkyne group can be contacted with an alkyl or aryl azide in the presence of Cu (I) and/or ruthenium catalyst to provide a Formula IIa compound with a PEG-triazole group.

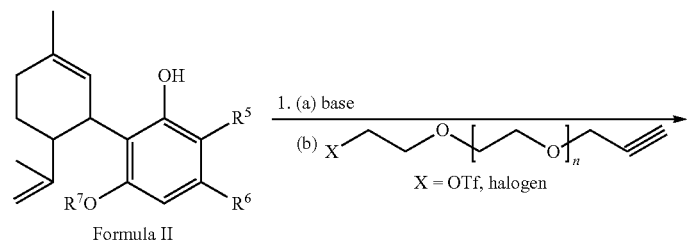

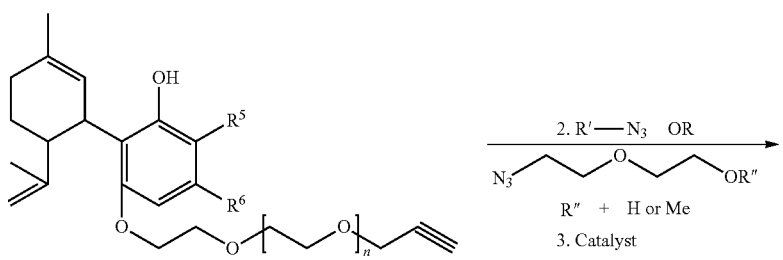

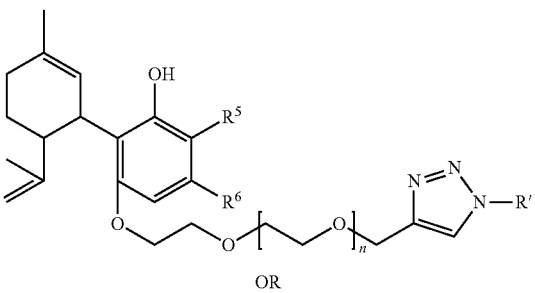

OR

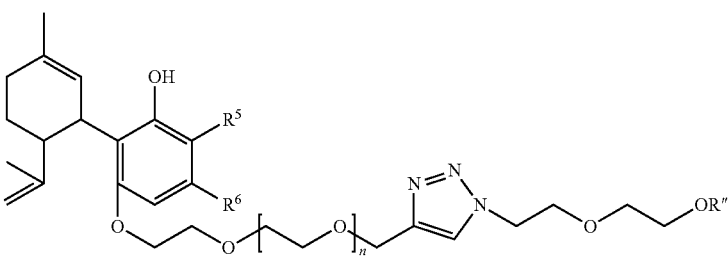

An alternate method for producing a Formula IIa compound with a PEG-triazole group is shown in Scheme 4. As illustrated, a Formula II compound is first contacted with a terminal azide containing PEG group to provide a Formula IIa compound with $R^8$ being a PEG-$N_3$. Such a Formula IIa compound is then further contacted with a suitable R"-alkyne group under conditions suitable for click cycloadditions of an alkyne with an azide to obtain a Formula IIa compound with a PEG-triazole group.

Scheme 4

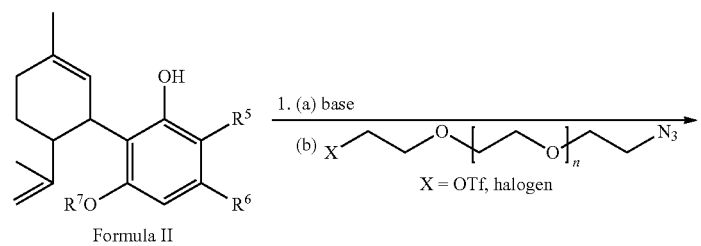

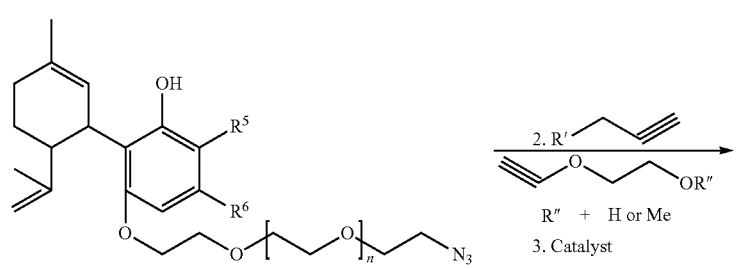

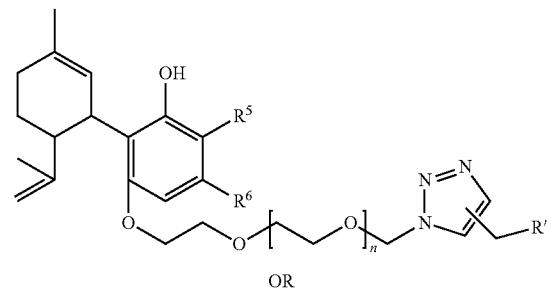
OR
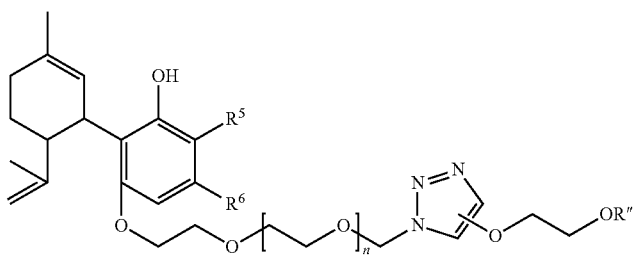
In yet another embodiment, the inventive method provides Formula IIa compounds where R8 is a -PEG-NH$_2$ or a —(C$_1$-C$_{10}$)alkyl-NH$_2$ group. An exemplary protocol for synthesizing such Formula IIa compounds is illustrated in Scheme 5.
Scheme 5
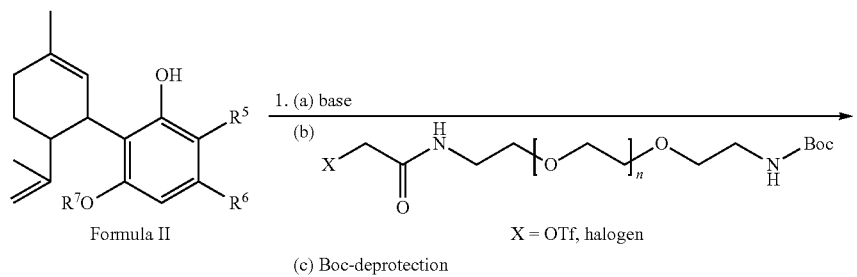
X = OTf, halogen
(c) Boc-deprotection
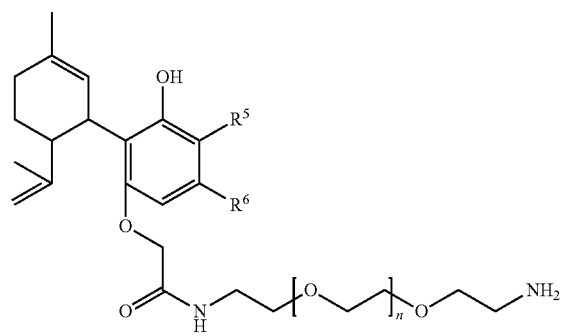

A similar synthetic methodology can be used to synthesize pegylated ethers of a Formula II compound. Thus, as shown in Scheme 6, contacting a Formula II compound with a suitably functionalized PEG group under basic conditions provides a Formula IIa compound.

Scheme 6

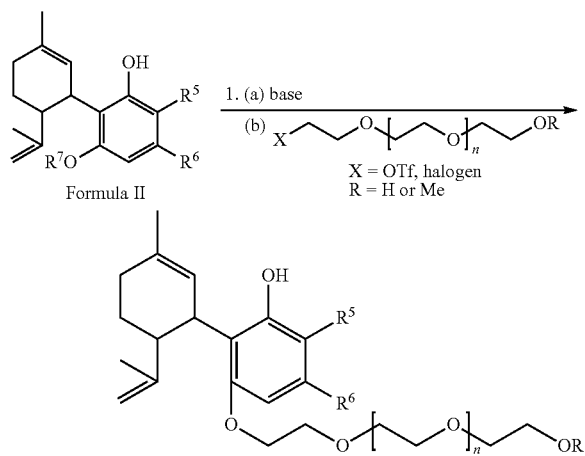

As described above, synthesis of a Formula II compound using the inventive method comprises the step of contacting a cannabinoid synthase enzyme with a Formula III compound. For the synthesis of Formula II compounds, the cannabinoid synthase is cannabidiolic acid (CBDA) synthase. These enzymes may be obtained from natural sources or may be obtained by using any suitable recombinant method, including the use of the PichiaPink™ Yeast Expression system described in U.S. Provisional Application No. 62/041,521, filed Aug. 25, 2014 and U.S. patent application Ser. No. 14/835,444, filed Aug. 25, 2015 which published as U.S. Publication No.: 2016-0053220 on Feb. 26, 2016, the contents of which applications are incorporated by reference in their entireties.

The synthesis of Formula II compounds in accordance with the method of the invention is carried out in the presence of a solvent. In one embodiment of the invention, the solvent used to produce a Formula II compound using the inventive method is an aqueous buffer, a non-aqueous solvent, or a mixture comprising an aqueous buffer and a non-aqueous solvent. Buffers typically used in the method of the invention are citrate buffer, phosphate buffer, HEPES, Tris buffer, MOPS, or glycine buffer. Illustrative non-aqueous solvents include without limitation dimethyl sulfoxide (DMSO), dimethyl formamide (DMF), or iso-propyl alcohol, β-cyclodextrin, and combinations thereof.

The solvent used to manufacture the Formula II compound can be a mixture of an aqueous buffer and a non-aqueous solvent. For such mixtures, the concentration of the non-aqueous solvent can vary between 10% and 50% (v/v), preferably the concentration of the non-aqueous solvent in the reaction mixture is 10%, 12%, 15%, 20%, 25%, 30%, 35%, 40%, 45%, or 50%. In one embodiment the concentration of the non-aqueous solvent in the reaction mixture is 30%. In another embodiment, the concentration of the non-aqueous solvent in the reaction mixture is 20%, or may vary between 10% and 20%, between 10% and 30%, or between 10% and 40%.

The pH of the reaction mixture may influence the synthesis of a Formula II compound using the inventive method. For example, the bioenzymatic synthesis of a Formula II compound can be performed at a pH in a range between 3.0 and 8.0. In one embodiment, the pH is in a range between 3.0 and 7.0, between 3.0 and 6.0, between 3.0 and 5.0, or between 3.0 and 4.0.

In yet another embodiment, the reaction to synthesize a Formula II compound by contacting a Formula III compound with a cannabinoid synthase is performed at a pH in a range between 3.8 and 7.2. According to another embodiment, the reaction is performed at a pH in a range between 3.5 and 8.0, between 3.5 and 7.5, between 3.5 and 7.0, between 3.5 and 6.5, between 3.5 and 6.0, between 3.5 and 5.5, between 3.5 and 5.0, or between 3.5 and 4.5.

Public interest in *Cannabis* as medicine has been growing, based in no small part on the fact that *Cannabis* has long been considered to have medicinal properties, ranging from treatment of cramps, migraines, convulsions, appetite stimulation and attenuation of nausea and vomiting. Recent studies have shown that cannabidiol, (CBD) is useful for the treating epilepsy, particularly, seizures in children suffering from Dravet Syndrome and Lennox-Gaustat Syndrome. However, CBD can convert to THC under acidic conditions or when brought in contact with heat. Because of the addictive and psychotic effects of THC the conversion of CBD to THC during the treatment of seizures is problematic, especially when CBD is used as a therapeutic for the treatment of pediatric seizures.

The present invention provides a method for treating neurological disorders using stable CBD derivatives as well as a method for increasing the physiological concentration of the inventive CBD derivatives.

According to one aspect, the invention provides a method for enhancing the physiological concentration of a Formula IVa compound by administering a Formula IVa compound to a subject.

Formula IVa

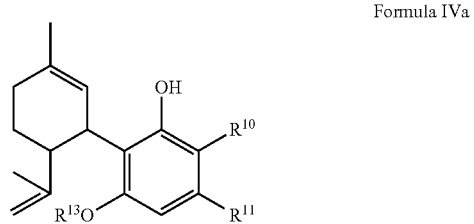

According to this method, the Formula IVa compound is obtained by contacting a Formula IV compound with a suitable Z—$R^{13}$ group.

Formula IV

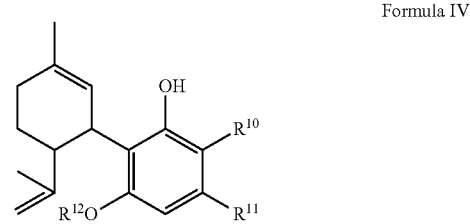

In one embodiment, for Formula IV and IVa compounds, substituent $R^{10}$ is —H, —COO$R^{14}$, or —(CH$_2$)$_n$COOH, and $R^{11}$ is an alkyl group, for example, an alkyl chosen from methyl, ethyl, propyl, butyl, pentyl, hexyl, and heptyl. In another embodiment, $R^{10}$ is —H, or —COO$R^{14}$, and $R^{11}$ is propyl, butyl, or pentyl. For such Formula IV and IVa compounds $R^{14}$ is —H or $(C_1$-$C_{10})$ alkyl.

For Formula IVa compounds $R^{13}$ is an optionally substituted $(C_1$-$C_{10})$alkyl, $(C_1$-$C_{10})$haloalkyl, optionally substituted $(C_3$-$C_{10})$aryl, optionally substituted $(C_3$-$C_{10})$cycloalkyl, optionally substituted $(C_3$-$C_{10})$aryl-$(C_1$-$C_{10})$ alkylene, optionally substituted $(C_3$-$C_{10})$cycloalkyl-$(C_1$-$C_{10})$alkylene, optionally substituted —$CH_2$—$CH_2$—[O—$CH_2$—$CH_2$—$]_m$O—$CH_2$—$CH_2$—$R^b$, optionally substituted —$(CHR^a)_q$—$NH_2$, or an optionally substituted —$(CHR^a)_q$—$NH^+_3X^-$ group.

For certain Formula IVa compounds $R^{13}$ is an optionally substituted $(C_1$-$C_{10})$alkyl. Exemplary alkyl groups include without limitation, methyl, ethyl, propyl, butyl, pentyl, hexyl, and heptyl.

For other Formula IVa compounds $R^{13}$ is an optionally substituted $(C_3$-$C_{10})$aryl, for example, phenyl, halophenyl, nitrophenyl, dinitrophenyl, benzyl, aminobenzyl and nitrobenzyl.

When $R^{13}$ in Formula IVa is —$CH_2$—$CH_2$—[O—$CH_2$—$CH_2$—$]_m$O—$CH_2$—$CH_2$—$R^b$, an optionally substituted —$(CHR^a)_q$—$NH_2$, or an optionally substituted —$(CHR^a)_q$—$NH^+_3X^-$ group, then $R^a$ is selected from the group consisting of —H, —OH, halogen, $(C_1$-$C_5)$ alkyl, and alkoxy and substituent $R^b$ is chosen from —OH, —O($C_1$-$C_5$) alkyl, —$(C_2$-$C_6)$ alkene, azide, and —$(C_2$-$C_6)$ alkyne.

For some Formula IVa compounds, substituent $R^{13}$ is —$CH_2$—$CH_2$—[O—$CH_2$—$CH_2$—$]_m$O—$CH_2$—$CH_2$— OH, —$CH_2$—$CH_2$—[O—$CH_2$—$CH_2$—$]_m$O—$CH_2$—$CH_2$—$N_3$, or —$CH_2$—$CH_2$—[O—$CH_2$—$CH_2$—$]_m$O—$CH_2$—C≡CH. For such compounds, subscript m is 1, 2, or 3.

For certain other Formula IVa compounds, substituent $R^{13}$ is —$CH_2$—$CH_2$—[O—$CH_2$—$CH_2$—$]_m$O—$CH_2$—$CH_2$—O—$CH_3$, —$CH_2$—$CH_2$—[O—$CH_2$—$CH_2$—$]_m$O—$CH_2$—$CH_2$—Br, or —$CH_2$—$CH_2$—[O—$CH_2$—$CH_2$—$]_m$O—$CH_2$—$CH_2$—Cl.

In one embodiment, substituent $R^{13}$ in Formula IVa is —$(CHR^a)_q$—$NH^+_3X^-$. For such compounds, substituent $R^a$ is —H, —OH, halogen, $(C_1$-$C_5)$ alkyl, or alkoxy and subscript "q" is 1, 2, or 3.

In one embodiment, substituent $R^{13}$ in Formula IVa is —$(CH_2)$—$NH^+_3X^-$, with "X" being a counter ion derived from a pharmaceutically acceptable acid.

For certain other Formula IVa compounds, substituent $R^{13}$ is —$(CH_2)_2$—$NH^+_3X^-$, —$(CH_2)_3$—$NH^+_3X^-$, or —$(CH_2)_4$—$NH^+_3X^-$. The biological concentration of the Formula IVa compound can be measure by any method known in the biochemical art. For example, the biological concentration of the Formula IVa compound can be measured in a blood or tissue sample that is obtained from a subject following the administration of the Formula IVa compound.

Any analytical technique, for example high performance reverse-phase liquid chromatography can be used to measure the biological concentration of the Formula IVa compound. The biological concentration of the Formula IVa compound is measured by comparing the area under a curve of a plasma sample to a standard curve that is generated prior to analysis of the biological sample.

In one embodiment, the concentration of the Formula IVa compound in the biological sample is in the range from 0.1 ng/mL to 50 ng/mL per milligram of the Formula IVa compound administered to the subject. According to another embodiment, the concentration of the Formula IVa compound in the biological sample is in the range from 0.1 ng/mL to 25 ng/mL per milligram of the Formula IVa compound administered to the subject, from 0.1 ng/mL to 15 ng/mL per milligram of the Formula IVa compound administered to the subject, from 0.1 ng/mL to 10 ng/mL per milligram of the Formula IVa compound administered to the subject, or from 0.1 ng/mL to 5 ng/mL per milligram of the Formula IVa compound administered to the subject.

According to the method of the invention, the biological concentration of the Formula IVa compound can be in the range from 2 ng/mL to 25 ng/mL per milligram of the Formula IVa compound administered to the subject, from 2 ng/mL to 20 ng/mL per milligram of the Formula IVa compound administered to the subject, from 2 ng/mL to 15 ng/mL per milligram of the Formula IVa compound administered to the subject, from 2 ng/mL to 10 ng/mL per milligram of the Formula IVa compound administered to the subject, or from 2 ng/mL to 5 ng/mL per milligram of the Formula IVa compound administered to the subject.

The anti-oxidant properties of cannabinoids makes these compounds candidate therapeutics for treating diseases and disorders associated with oxidative stress. Cannabinoids also exert neuroprotective effects, for example, by limiting neurological damage following ischemic insults, such as from strokes and trauma, or in the treatment of neurodegenerative diseases, such as Alzheimer's disease, Parkinson's disease and HIV dementia.

In this regard, the non-psychoactive cannabinoids, such as cannabidoil or derivatives of cannabidiol according to Formula I, IIa, IVa or V, are particularly advantageous to use because they avoid toxicity that is encountered with psychoactive cannabinoids, have increased bio-stability and thus, greater bioavailability at doses useful according to a method of the present invention.

In the context of this disclosure, the phrases "oxidative associated diseases" or "diseases and disorders associated with oxidative stress" refer to pathological conditions that result at least in part from the production of or exposure to free radicals, particularly oxyradicals, or reactive oxygen species. It is evident to those of skill in the art that most pathological conditions are multifactorial, and that assigning or identifying the predominant causal factors for any particular condition is frequently difficult.

In one embodiment, therefore, the invention provides a method for treating a neurological condition, by administering a therapeutically effective amount of a Formula V compound to a subject in need of treatment.

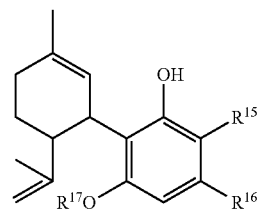

Formula V

For Formula V compounds, $R^{15}$ is —H, —$COOR^{18}$, or —$(CH_2)_n$COOH, and substituent $R^{16}$ is selected from the group consisting of methyl, ethyl, propyl, butyl, pentyl, hexyl, and heptyl.

Substituent $R^{17}$ in Formula V is group chosen from optionally substituted $(C_1$-$C_{10})$ alkyl, $(C_1$-$C_{10})$ haloalkyl, optionally substituted $(C_3$-$C_{10})$aryl, optionally substituted $(C_3$-$C_{10})$cycloalkyl, optionally substituted $(C_3$-$C_{10})$aryl-$(C_1$-$C_{10})$alkylene, optionally substituted $(C_3$-$C_{10})$cycloalkyl-$(C_1$-$C_{10})$alkylene, optionally substituted —$CH_2$—$CH_2$—[O—$CH_2$—$CH_2$—$]_m$O—$CH_2$—$CH_2$—$R^b$, optionally substituted —(CHR$^a$)$_q$—NH$_2$, or an optionally substituted —(CHR$^a$)$_q$—NH$^+_3$X$^-$.

When R$^{17}$ is —CH$_2$—CH$_2$—[O—CH$_2$—CH$_2$—]$_m$O—CH$_2$—CH$_2$—R$^b$, —(CHR$^a$)$_q$—NH$_2$, or —(CHR$^a$)$_q$—NH$^+_3$X$^-$, R$^3$ is —H, —OH, halogen, (C$_1$-C$_5$) alkyl, and alkoxy and substituent R$^b$ is —OH, —O(C$_1$-C$_5$) alkyl, —(C$_2$-C$_6$) alkene, azide, or —(C$_2$-C$_6$) alkyne.

Cannabidiol Prodrugs

Cannabidiol (CBD) which is non-psychoactive is reported to undergo conversion to the psychoactive cannabinoid THC when administered orally. In fact, recent studies suggest that CBD forms Δ$^9$-THC, Δ$^8$-THC, 8-hydroxy-iso-hexahydrocannabinol (8-OH-iso-HHC), and 9α-hydroxy hexahydrocannabinol (9α-OH-HHC), in the presence of simulated gastric fluid (SGF). See Forensic Toxicol., Wanatabe, K. et al., (2007), Vol. 25, 16-21. Scheme 7 illustrates cannabinoids obtained from CBD in the presence of SGF.

eases, and epilepsy. Clinical studies with CBD, particularly in patients with epilepsy, have generated interest in its medical application as a candidate therapeutic for treating epilepsy, particularly in pediatric patients with Dravet Syndrome, Angelman syndrome, benign rolandic epilepsy, childhood absence epilepsy, juvenile myoclonic epilepsy, West Syndrome, and Lennox-Gastaut Syndrome.

However, recent studies using CBD as a therapeutic for treating pediatric epilepsy patients revealed high incidence of adverse effects after oral administration of CBD. See Cannabis and Cannabinoid Research, Vol. 1.1, (2016), p. 102-112. For example, greater than 44% of the patients receiving CBD orally showed somnolence, and the incidence of fatigue in pediatric patients was relatively high after the oral administration of CBD. The most likely explanation for the observed adverse effects, according to

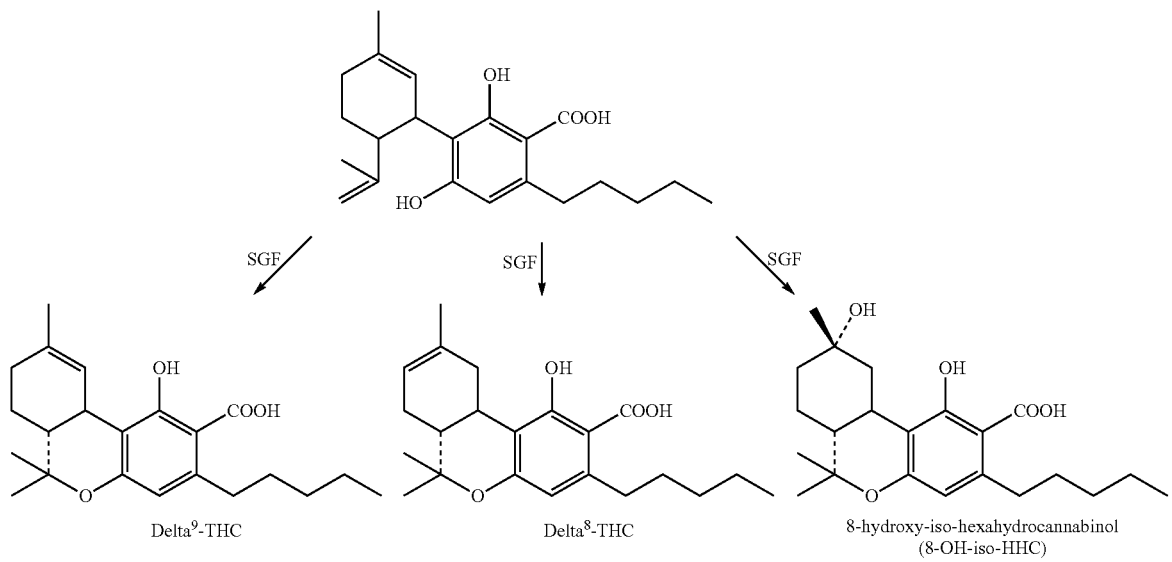

Scheme 7

Delta$^9$-THC    Delta$^8$-THC    8-hydroxy-iso-hexahydrocannabinol (8-OH-iso-HHC)

SGF = simulated gastric fluid

Without ascribing to a specific hypothesis, it is believed that the formation of Δ$^9$-THC, Δ$^8$-THC, 8-hydroxy-iso-hexahydrocannabinol (8-OH-iso-HHC) from CBD most likely is attributed to the acidic environment of the gut. The formation of these compounds is undesired, especially because Δ$^9$-THC, Δ$^8$-THC, 8-hydroxy-iso-hexahydrocannabinol (8-OH-iso-HHC), and 9α-hydroxy hexahydrocannabinol (9α-OH-HHC), by contrast to CBD, potentiate adverse physiological effects such as catalepsy, hypothermia and antinociception effects.

Considerable interest in the medical and pharmaceutical community fuels the exploitation of the non-psychoactive cannabinoid CBD as a therapeutic for treating a variety of diseases states. For example, CBD has shown antiemetic, anticonvulsant, anti-inflammatory, and antipsychotic properties in animal studies. Clinical trials conducted with a variety of disease states, among them multiple sclerosis, schizophrenia, bipolar mania, social anxiety disorder, insomnia, Huntington's disease, and epilepsy, show that CBD has a positive safety profile, and that CBD is effective as a therapeutic for treating patients with inflammation, diabetes, cancer, affective disorders, neurodegenerative disthe authors of this study, is the degradation and cyclization of CBD to THC in the acidic environment of the gut.

The present invention prevents these adverse effects by providing biostable prodrugs of CBD. Specifically, the invention provides (C$_1$-C$_{10}$)alkyl, (C$_1$-C$_{10}$)haloalkyl, an optionally substituted (C$_3$-C$_{10}$)cycloalkyl, an optionally substituted (C$_3$-C$_{10}$)cycloalkyl-(C$_1$-C$_{10}$)alkylene, an optionally substituted —CH$_2$—CH$_2$—[O—CH$_2$CH$_2$—]$_m$O—CH$_2$—CH$_2$—R$^b$, an optionally substituted —(CHR$^a$)$_q$—NH$_2$, or an optionally substituted —(CHR$^a$)$_q$—NH$^+_3$X$^-$ ethers of CBD.

For such prodrugs, substituent R$^a$ is selected from the group consisting of —H, —OH, halogen, (C$_1$-C$_5$) alkyl, and alkoxy. Substituent R$^b$ is selected from the group consisting of —OH, —O(C$_1$-C$_5$) alkyl, —(C$_2$-C$_6$) alkene, azide, and —(C$_2$-C$_6$) alkyne.

The inventive ether prodrugs were more stable than CBD in the presence of an acidic medium. Data from stability studies of two exemplary CBD ether prodrugs, namely, the methyl ether and the difluoromethyl ether prodrugs in the presence of SGF, microsomes, buffers of different pH's, and human S-9 hepatic fraction show the inventive prodrugs to be significantly more stable than CBD.

Pharmaceutical Compositions

The compounds of Formula I, IIa, IVa or Formula V produced in accordance with the inventive methods are administered to a patient or subject in need of treatment either alone or in combination with other compounds having similar or different biological activities. For example, the compounds and compositions of the compounds of the invention are administered in a combination therapy, i.e., either simultaneously in single dosage forms or in separate dosage forms within hours or days of each other and a second therapeutic agent. Examples of such combination therapies include administering the compositions and compounds produced by the inventive methods with other agents used to treat glaucoma, epilepsy, AIDS wasting, neuropathic pain, treatment of spasticity associated with multiple sclerosis, fibromyalgia and chemotherapy-induced nausea. Alternatively, the inventive cannabinoid derivatives are administered as candidate neuroprotective agents to a subject diagnosed or at a risk of developing a neurological condition, such as dementia, Alzheimers Disease, or schizophrenia.

Thus, the invention provides a pharmaceutical composition comprising a cannabinoid derivative or a pharmaceutically acceptable salt, solvate, or stereoisomer in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

The inventive compositions can be administered orally, topically, parenterally, by inhalation or spray or rectally in dosage unit formulations. The term parenteral as used herein includes subcutaneous injections, intravenous, intramuscular, intrasternal injections or infusion techniques.

Suitable oral compositions in accordance with the invention include without limitation tablets, troches, lozenges, aqueous or oily suspensions, dispersible powders or granules, emulsion, hard or soft capsules, syrups or elixirs.

Encompassed within the scope of the invention are pharmaceutical compositions suitable for single unit dosages that comprise at least one of a Formula I, IIa, IVa, or V compound or a pharmaceutically acceptable solvate, or stereoisomer and a pharmaceutically acceptable carrier.

Inventive compositions suitable for oral use may be prepared according to any method known to the art for the manufacture of pharmaceutical compositions. For instance, liquid formulations of a Formula I, IIa, IVa, or V compound, can contain one or more agents selected from the group consisting of sweetening agents, flavoring agents, coloring agents and preserving agents in order to provide pharmaceutically elegant and palatable preparations of the inventive prodrug.

For tablet compositions, the active ingredient in admixture with non-toxic pharmaceutically acceptable excipients is used for the manufacture of tablets. Exemplary of such excipients include without limitation inert diluents, such as calcium carbonate, sodium carbonate, lactose, calcium phosphate or sodium phosphate; granulating and disintegrating agents, such as corn starch, or alginic acid; binding agents, for example starch, gelatin or acacia, and lubricating agents, such as magnesium stearate, stearic acid or talc. The tablets can be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions the active agent, such as a Formula I, IIa, IVa, or V compound, is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally occurring phosphatide, for example, lecithin, polyoxyethylene stearate, heptadecaethyleneoxycetanol, polyoxyethylene sorbitol monooleate, polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Syrups and elixirs can be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, or an aqueous suspension. This suspension may be formulated according to the known art using those suitable dispersing or wetting agents and suspending agents. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compositions for parenteral administrations are administered in a sterile medium. Depending on the vehicle used and the concentration of the Formula I, IIa, IVa, or V compound in the formulation, the parenteral formulation can either be a suspension or a solution containing dissolved drug. Adjuvants such as local anesthetics, preservatives and buffering agents can also be added to parenteral compositions.

The total amount by weight of a Formula I, IIa, IVa, or V compound of the invention in a pharmaceutical composition is from about 0.1% to about 95%. By way of illustration, the amount of a Formula I, IIa, IVa, or V compound by weight of the pharmaceutical composition, such as a Formula I, Formula IIa, Formula IVa, or Formula V compound of the invention can be about 0.1%, about 0.2%, about 0.3%, about 0.4%, about 0.5%, about 0.6%, about 0.7%, about 0.8%, about 0.90%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.90%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.90%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.90%, about 90%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

In one embodiment, the pharmaceutical composition comprises a total amount by weight of a Formula I, IIa, IVa, or V compound, of about 1% to about 10%; about 2% to about 10%; about 3% to about 10%; about 4% to about 10%; about 5% to about 10%; about 6% to about 10%; about 7% to about 10%; about 8% to about 10%; about 9% to about 10%; about 1% to about 90%; about 2% to about 9%; about 3% to about 9%; about 4% to about 9%; about 5% to about 90%; about 6% to about 9%; about 7% to about 9%; about 8% to about 9%; about 1% to about 8%; about 2% to about 8%; about 3% to about 8%; about 4% to about 8%; about 5% to about 8%; about 6% to about 8%; about 7% to about 8%; about 1% to about 7%; about 2% to about 7%; about 3% to about 7%; about 4% to about 7%; about 5% to about 7%; about 6% to about 7%; about 1% to about 6%; about 2% to about 6%; about 3% to about 6%; about 4% to about 6%; about 5% to about 6%; about 1% to about 5%; about 2% to about 5%; about 3% to about 5%; about 4% to about 5%; about 1% to about 4%; about 2% to about 4%; about 3% to about 4%; about 1% to about 3%; about 2% to about 3%; or about 1% to about 2%.

EXAMPLES

Synthesis of Alkyl and Haloalkyl Ethers
The alkyl and haloalkyl ethers according to Formula I, IIa, IVa, or V are obtained as follows:
1. Methyl Ethers
Simple methyl ethers are produced by contacting a THF or dichloromethane (DCM) solution of the phenol starting material, for example a Formula II or IV compound, with an anhydrous THF solution of diazomethane under inert conditions. Generally, a slight excess of diazomethane is added, about 1.2-1.5 equivalents, and the reaction is quenched by evaporation of the organic solvent once complete.

Alternatively, methyl ethers are produced by contacting a THF or acetonitrile solution of Formula II or IV compound with sodium hydroxide, followed by contact with dimethylsulfate. Progress of the reaction will be monitored by TLC, and the crude product can be purified by silica gel flash column chromatography if necessary.
2. Alkyl Ethers
Alkyl ethers according to Formula I, IIa, IVa, or V are obtained by contacting a DCM/DMF solution of a Formula II or IV compound with sodium hydride followed by the addition of a slight excess (1.2-1.5 equivalents), of the desired alkyl halide, for example the desired alkyl iodide or alkyl bromide. Reaction progress is monitored by TLC, and the reaction quenched by the addition of brine followed by extraction of the aqueous phase with DCM or ethyl acetate. The crude product is purified by silica gel flash column chromatography if necessary.

Alternatively, alkyl ethers are obtained by contacting a solution of a Formula II or IV compound with the desired alkyl triflate, followed by purification of the crude product by silica gel flash column chromatography.
3. Haloalkyl Ethers
Synthesis of haloalkyl ethers is carried out by protocols described above for alkyl ethers. For instance, synthesis of difluoroalkyl ethers (e.g., difluoromethyl ethers) according to Formula I, IIa, IVa, or V is carried out by contacting an acetonitrile or THF solution of a Formula II or IV compound with an aqueous solution of KOH or NaOH at room temperature. After stirring for about 5 min., add 1.5-2.0 equivalents of the triflic acid ester of difluoromethanol ($HCF_2$—OTf).

Monitor formation of the $HCF_2$-ether by TLC and quench the reaction by the drop-wise addition of water. The aqueous phase is then extracted with diethyl ether or ethyl acetate and the combined organic layers containing the desired difluoromethyl ether product is purified, if needed, by column chromatography.
4. Aryl Ethers
Synthesis of aryl ethers, such as benzyl or 4-nitrobenzyl ethers is accomplished by contacting an acetonitrile or THF solution of a Formula II or IV compound with an aqueous solution of KOH or NaOH at room temperature. The resultant phenoxide anion is then contacted with benzyl bromide, (Boc)-4-aminobenzyl bromide, or 4-nitrobenzyl bromide to produce a benzyl ether according to Formula I, IIa, IVa, or V.

Alternatively, as illustrated in Scheme 2, benzyl ethers can be synthesized by contacting a Formula II or IV compound with benzyl trichloroacetimidate under acidic conditions or a solution of a Formula II or IV compound with a toluene solution of 2-benzyloxy-N-methylpyridinium triflate under neutral conditions as illustrated in Scheme 2 above. The reaction mixture can be heated to promote ether formation.

Benzyl ethers according to Formula I, IIa, IVa, or V are also obtained by contacting a Formula II or IV compound with 2-benzyloxy pyridine, and magnesium oxide in toluene. The resultant mixture is cooled to 0 C prior to the addition of 1.0 equivalents of methyl triflate. The cold reaction mixture is permitted to warm to room temperature and then heated under reflux to about 90 C. Following ether synthesis, the reaction is diluted with water and the crude product is extracted using diethyl ether or ethyl acetate. The combined organic layers containing the crude product may be purified prior to use.
Biological Stability Studies
The stability of the inventive compounds in serum, buffer and in gut medium was tested. The half-life ($t_{1/2}$) of de-etherification was calculated from such stability experiments. Additionally, the kinetics of cyclization of a CBD or CBDA derivative according to Formula I, IIa, IVa, or, V of the invention to THC or THCA will be determined.

CBD methyl ether and CBD difluoromethyl ether were synthesized using a synthetic protocol described above and the identities of the desired ether products were confirmed by nuclear magnetic resonance spectroscopy as well as HPLC-MS. CBD methyl and/or CBD difluoromethyl ethers were incubated in individual eppendorf tubes in the following mediums: (a) simulated gastric fluid (SGF) with and without pepsin; (b) microsomal extract; (c) S9 fraction (hepatic); (d) Plasma; (e) Teorell-Stenhagen Buffer at pH 3.5, 4.5, 5.5, 6.5, 7.5, and 8.5; and (f) simulated intestinal fluid (SIF) with and without pancreatin. Each incubation mixture contained up to 0.5% of an organic solvent. DMSO is the organic solvent when SGF and Teorell-Stenhagen Buffer was used and acetonitrile is the organic solvent for incubation mixtures in microsomal extract, S9 fraction, and plasma. The concentration of CBD methyl and/or CBD difluoromethyl ether is 10 µM for stability studies in SGF and Teorell-Stenhagen Buffer. However, the concentration of CBD methyl and/or CBD difluoromethyl ether is 1 µM for stability studies in microsomal extract, S9 fraction, and plasma.

Stability studies were performed by incubating CBD methyl ether and/or CBD difluoromethyl ether at 37° C. in the desired medium. Aliquots were taken at fixed intervals of time, typically at 0, 5, 10, 15, 30, and 45 minutes, or at fixed intervals of 1 h, 1.5 h, 2 h, 4 h, 6 h, 8 h, 24 h, and 48 hours. At each interval of time, two aliquots of each sample were collected. Each aliquot was extracted with ethyl acetate. The ethyl acetate layer was evaporated using a stream of nitrogen gas and the resulting residue was dissolved in 1:1 mixture of 0.1% aqueous HOAc and acetonitrile and analyzed by reverse-phase HPLC-MS.

Table 1 illustrates the results of a stability study in SGF with and without pepsin as well as in simulated intestinal fluid (SIF) with and without pancreatin. The half-life of de-etherification (conversion of CBD ether prodrug to CBD) for the methyl and difluoromethyl ethers was greater than 400 min. In comparison, greater than 85% of the CBD cyclized to mixture of $\Delta^8$-THC and $\Delta^9$-THC in about 60 minutes.

TABLE 1

Stability In SGF

| Compound ID | Batch Name | SGF $t_{1/2}$ (min) | SGF No Pepsin $t_{1/2}$ (min) | SIF $t_{1/2}$ (min) | SIF No Pancreatin $t_{1/2}$ (min) |
|---|---|---|---|---|---|
| CBD Methyl Ether | JYA-U-155-3 | >400 | >400 | >400 | >400 |
| CBD Difluoromethyl Ether | JYA-U-159-6 | >400 | >400 | >400 | >400 |

Assay Conditions:
Test Compound Concentration is 10 µM;
percentage of organic solvent is 0.5% DMSO;
incubation times - 0, 15, 30, 60, and 90 min.;
37° C.

The composition of buffer containing SGF or SIF is as follows. Buffer Composition: (A) SGF: 1 g NaCl, 1.6 g Pepsin*, 3.5 mL HCL, 500 mL water, pH 1.2 (* two separate solutions were prepared, one with pepsin and one without pepsin). (B) SIF: 3.4 g monobasic potassium phosphate, 38.5 mL 0.2M NaOH, 5 g pancreatin*, 875 mL water, pH 6.8 (* two separate solutions were prepared, one with pancreatin and one without pancreatin).

Table 2 illustrates the results of a stability study in buffers at different pH's. The half-life of de-etherification for CBD methyl ethers was greater than 72 hours while the half-life of de-etherification for the corresponding difluoromethyl ether is between 8 h to 14 hours.

TABLE 2

Chemical Stability Assay - Teorell-Stenhagen Buffer

| | | Teorell-Stenhagen Buffer | | | | | |
|---|---|---|---|---|---|---|---|
| Compound ID | Batch Name | pH 3.5 $t_{1/2}$ (h) | pH 4.5 $t_{1/2}$ (h) | pH 5.5 $t_{1/2}$ (h) | pH 6.5 $t_{1/2}$ (h) | pH 7.5 $t_{1/2}$ (h) | pH 8.5 $t_{1/2}$ (h) |
| CBD Methyl Ether | JYA-U-155-3 | >72 | >72 | >72 | >72 | >72 | >72 |
| CBD Difluoromethyl Ether | JYA-U-159-6 | 10 | 14 | 11 | 11 | 11 | 8 |

Assay Conditions: Test Compound Concentration is 10 µM; percentage of organic solvent is 0.5% DMSO; incubation times - 0, 1, 10, 4, 6, 8, 24, 48, and 72 hours; 20° C.; Teorell-Stenhagen Buffer Composition: 0.033M citric acid, 0.033M sodium phosphate, 0.057M boric acid in water The stability of CBD methyl ether and CBD difluoromethyl ether in the hepatic S9 fraction is illustrated in Table 3. Both the methyl and difluoromethyl ethers were reasonably stable in S9 fraction with half-lives for de-etherification being about 5 hours for the methyl ether and about 3 hours for the difluoromethyl ether. In comparison, testosterone had a half-life of degradation of about 29 minutes.

Intrinsic clearance (CLint) is clearance of drug by the livers if the drug is not bound to serum proteins or dependent on blood flow for delivery to the livers. Intrinsic clearance (CLint) is influenced by the affinity of the drug for its metabolizing liver enzyme and the number of enzymes present. CLint is subject to saturation and governed by Michaelis-menten (non-linear) elimination kinetics. Intrinsic clearance can be constant at low concentration, but progressively decreases as enzyme sites become saturated. Drugs with a strong affinity for their metabolizing enzymes or for which there are a large number of enzymes would be more efficiently extracted by the liver and thus, have a high extraction ratio ($E_H$).

The hepatic extraction ratio $E_H$ is a good measure of expected first-pass metabolic clearance from liver (typical first pass after oral administration). The hepatic extraction ratio ($E_h$) is represented as follows:

$$E_h = CL_H/Q_H$$

Hepatic clearance ($CL_H$) is the volume of blood that is cleared of drug per unit time by the liver, and $Q_H$ is the rate of blood flow to the liver.

The hepatic extraction ratio $E_H$ is particularly useful for separating compounds into low/medium/high metabolic stability categories. Unlike in vitro intrinsic microsomal clearance ($CL_{int}$), $E_H$ is species-nonspecific, because in its calculation species differences like liver weight, body weight, liver blood flow, etc. are normalized out, so $E_H$ values can be directly compared across species.

As illustrated in Table 3, both CBD ethers have a lower hepatic extraction ratio compared to testosterone, and are therefore considered to be less susceptible to metabolic degradation and elimination by the liver due to a first pass effect. Therefore, such CBD ethers are candidate therapeutics for oral formulations.

TABLE 3

S9 Intrinsic Clearance Assay

| | | Human S9* | | |
|---|---|---|---|---|
| Compound ID | Batch Name | $t_{1/2}$ (min) | $CL_{int}$ (μL/min/mg) | $E_H$ |
| CBD Methyl Ether | JYA-U-155-3 | 286 | 1.9 | 21% |
| CBD Difluoromethyl Ether | JYA-U-159-6 | 173 | 3.2 | 31% |
| Testosterone** | | 29 | 47 | 87% |

Assay Conditions:
Test Compound Concentration is 1 μM;
microsomal protein concentration is 1.25 mg/mL;
percentage of organic solvent is 0.5% acetonitrile;
incubation times - 0, 5, 10, 15, 30 and 45 min.;
pH = 7.4;
37° C.;
co-factors - NADPH, UDPGA, and PAPS.

In vitro intrinsic microsomal clearance studies were performed to understand the metabolic fate of CBD ethers, as well as to identify metabolites produced by the degradation of the inventive CBD ethers.

The liver is the most important site of drug metabolism in the body. Approximately 60% of marketed compounds are cleared by hepatic CYP-mediated metabolism. See *Drug Metab. Dispos.*, 27(11) (1999) 1350. Liver microsomes are a subcellular fraction of hepatocytes, and they contain membrane bound drug metabolizing enzymes. Microsomes can be used to determine the in vitro intrinsic clearance of a compound. The use of species-specific microsomes can be used to enable an understanding of interspecies differences in drug metabolism.

As Table 4 shows, the methyl and difluoromethyl ethers of CBD are relatively stable in liver microsome extract. Both CBD ethers have a lower hepatic extraction ratio compared to testosterone, and are therefore considered to be less susceptible to hepatic clearance.

TABLE 4

Microsomal Intrinsic Clearance Assay

| | | HLM | | |
|---|---|---|---|---|
| Compound ID | Batch Name | $t_{1/2}$ (min) | $CL_{int}$ (μL/min/mg) | $E_H$ |
| CBD Methyl Ether | JYA-U-155-3 | 80 | 8.7 | 26% |
| CBD Difluoromethyl Ether | JYA-U-159-6 | 77 | 9.0 | 26% |
| Testosterone (Positive control) | | 10 | 69 | 73% |

Assay Conditions:
Test Compound Concentration is 1 μM;
microsomal protein concentration is 1 mg/mL;
percentage of organic solvent is 0.5% acetonitrile;
incubation times - 0, 5, 10, 15, 30 and 45 min.;
pH = 7.4;
37° C.

The methyl and difluoromethyl ethers of CBD were stable to degradation in plasma. The half-life of degradation as measured by LC-MS for both ethers was greater than 400 minutes. This data is illustrated in Table 5.

TABLE 5

Plasma Stability Assay

| Compound ID | Batch Name | Human $t_{1/2}$ (min) |
|---|---|---|
| CBD Methyl Ether | JYA-U-155-3 | >400 |
| CBD Difluoromethyl Ether | JYA-U-159-6 | >400 |

The stability studies show that protecting the hydroxyl group of CBD as an alkyl or haloalkyl ether provides a compound that is more stable to degradation and cyclization to THC in the gastrointestinal tract. Thus, CBD ethers are suitable candidate therapeutics for oral formulations used in the treatment of diseases, such as epilepsy, in pediatric patients.

The methyl ether and difluoromethyl ether of CBD showed good solubility in phosphate buffered saline (pH 7.4). As Table 6 shows, both CBD ethers dissolved in PBS to provide micromolar concentration solutions that are suitable for pharmaceutical compounding.

TABLE 6

Solubility Assay - PBS

| Compound ID | Batch Name | λ (nm) | Solubility (μM) in PBS 7.4 | Solubility (μM) in T-S 7.5 |
|---|---|---|---|---|
| CBD Methyl Ether | JYA-U-155-3 | 280 | 8.4 | 22 |
| CBD Difluoromethyl Ether | JYA-U-159-6 | 280 | 7.0 | 9.7 |

We claim:

1. A compound according to Formula I or a pharmaceutically acceptable salt, solvate, or stereoisomer thereof:

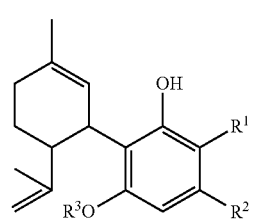

Formula I wherein
$R^1$ is —H, —COOR$^4$, or —(CH$_2$)$_n$COOH;
$R^2$ is selected from the group consisting of methyl, ethyl, propyl, butyl, pentyl, hexyl, and heptyl;
$R^3$ is selected from the group consisting of (C$_1$-C$_{10}$)haloalkyl, (C$_3$-C$_{10}$)cycloalkyl, (C$_3$-C$_{10}$)cycloalkyl-(C$_1$-C$_{10}$)alkylene, —CH$_2$—CH$_2$—[O—CH$_2$—CH$_2$—]$_m$O—CH$_2$—CH$_2$—R$^b$, and —(CHR$^a$)$_q$—NH$^+_3$X$^-$;
$R^a$ is selected from the group consisting of —H, —OH, halogen, (C$_1$-C$_5$) alkyl, and alkoxy;
$R^b$ is selected from the group consisting of —OH, —O(C$_1$-C$_5$) alkyl, —(C$_2$-C$_6$) alkene, azide, and —(C$_2$-C$_6$) alkyne;
$R^4$ is —H or (C$_1$-C$_{10}$) alkyl;
X is a counter ion derived from a pharmaceutically acceptable acid; and
n, m and q are each independently 0, 1, 2, 3, 4, 5, 6, 7, 8, 9, or 10.

2. The compound according to claim 1, wherein $R^1$, is —H and $R^2$ is propyl or pentyl.

3. The compound according to claim 1, wherein $R^3$ is selected from the group consisting of $(C_1$-$C_{10})$haloalkyl, —$CH_2$—$CH_2$—[O—$CH_2$—$CH_2$—]$_m$O—$CH_2$—$CH_2$—OH, and —$(CH_2)_q$—$NH^+_3X^-$.

4. The compound according to claim 3, wherein $R^3$ is $(C_1$-$C_{10})$haloalkyl.

5. The compound according to claim 4, wherein $R^3$ is selected from the group consisting of fluoromethyl, difluoromethyl, trifluoromethyl, fluoroethyl, fluoropropyl, fluorobutyl, fluoro-t-butyl, 1,1,-difluoro-t-butyl, 1,2-difluoro-t-butyl, 1,2,3-trifluoro-t-butyl, and 1,1,2-trifluoro-t-butyl.

6. The compound according to claim 3, wherein $R^3$ is —$(CH_2)_2$—[O—$CH_2$—$CH_2$—]$_m$O—$(CH_2)_2$—OH and m is 2 or 3.

7. The compound according to claim 3, wherein $R^3$ is —$(CHR^a)_q$—$NH^+_3X^-$ and $R^a$ is —H.

8. The compound according to claim 7, wherein $R^3$ is —$(CH_2)_4$—$NH^+_3X^-$, —$(CH_2)_5$—$NH^+_3X^-$, —$(CH_2)_6$—$NH^+_3X^-$, or —$(CH_2)_7$—$NH^+_3X^-$.

9. A method for producing a compound according to Formula IIa or a pharmaceutically acceptable salt, solvate, or stereoisomer thereof,

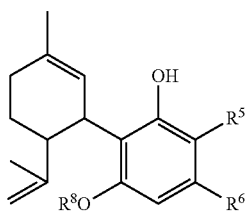

Formula IIa comprising:
(i) contacting a compound of Formula III

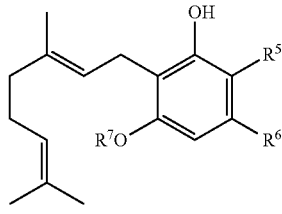

Formula III with a cannabinoid synthase in the presence of a solvent to produce a compound according to Formula II

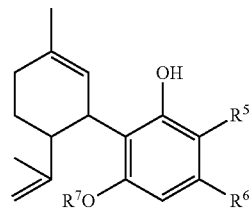

Formula II and then
(ii) contacting the Formula II compound with a suitable Y—$R^8$ group to produce a compound according to Formula IIa;

wherein
$R^5$ is —H, —$COOR^9$, or —$(CH_2)_n$COOH;
$R^6$ is selected from the group consisting of methyl, ethyl, propyl, butyl, pentyl, hexyl, and heptyl;
$R^7$ is —H;
$R^8$ is selected from the group consisting of $(C_1$-$C_{10})$ alkyl, $(C_1$-$C_{10})$haloalkyl, $(C_3$-$C_{10})$aryl, $(C_3$-$C_{10})$cycloalkyl, $(C_3$-$C_{10})$aryl-$(C_1$-$C_{10})$alkylene, $(C_3$-$C_{10})$cycloalkyl-$(C_1$-$C_{10})$alkylene, —$CH_2$—$CH_2$—[O—$CH_2$—$CH_2$—]$_m$O—$CH_2$—$CH_2$—$R^b$, —$(CHR^a)_q$—$NH_2$, and —$(CHR^a)_q$—$NH^+_3X^-$;
$R^a$ is selected from the group consisting of —H, —OH, halogen, $(C_1$-$C_5)$ alkyl, and alkoxy;
$R^b$ is selected from the group consisting of —OH, —O$(C_1$-$C_5)$ alkyl, —$(C_2$-$C_6)$ alkene, azide, and —$(C_2$-$C_6)$ alkyne;
$R^9$ is —H or $(C_1$-$C_{10})$ alkyl;
X is a counter ion derived from a pharmaceutically acceptable acid;
Y is a leaving group; and
n, m and q are each independently 0, 1, 2, 3, 4, 5, 6, 7, 8, 9, or 10.

10. The method according to claim 9, wherein $R^5$ is —H and $R^6$ is propyl or pentyl.

11. The method according to claim 9, wherein $R^5$ is —$COOR^9$ and $R^9$ is —H.

12. The method according to claim 11, further comprising the step of de-carboxylation by contacting a solution of the Formula II compound to heat or by exposing a solution of the Formula II compound to UV-light.

13. The method according to claim 9, wherein Y is selected from the group consisting of halogen, triflate, mesylate, —$OBF_3$, maleimide, and tosylate.

14. The method according to claim 9, wherein $R^8$ is $(C_1$-$C_{10})$ alkyl, $(C_3$-$C_{10})$aryl, $(C_3$-$C_{10})$aryl-$(C_1$-$C_{10})$alkylene, —$CH_2$—$CH_2$—[O—$CH_2$—$CH_2$—]$_m$O—$CH_2$—$CH_2$—OH, —$(CHR^a)_q$—$NH_2$, and —$(CHR^a)_q$—$NH^+_3X^-$.

15. The method according to claim 14, wherein $R^8$ is $(C_1$-$C_{10})$ alkyl.

16. The method according to claim 15, wherein $R^8$ is methyl, ethyl, propyl, butyl, t-butyl, pentyl, hexyl, or heptyl.

17. The method according to claim 14, wherein $R^8$ is —$(CH_2)_2$—[O—$CH_2$—$CH_2$—]$_m$O—$(CH_2)_2$—OH and m is 2 or 3.

18. The method according to claim 14, wherein $R^8$ is —$(CHR^a)_q$—$NH^+_3X^-$, $R^a$ is —H, and q is 4, 5, 6, or 7.

19. The method of claim 9, wherein the cannabinoid synthase is a cannabidiolic acid synthase (CBDA synthase).

20. A method for enhancing the biological concentration of a Formula IVa compound,

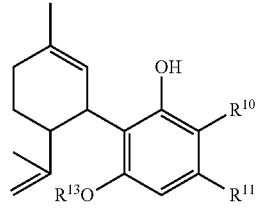

Formula IVa comprising administering the Formula IVa compound to a subject;
wherein, the compound according to Formula IVa is obtained by contacting a Formula IV compound with a suitable Z—$R^{13}$ group;

Formula IV

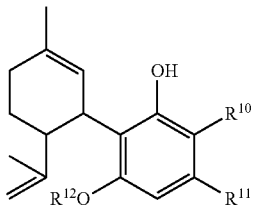

wherein
$R^{10}$ is —H, —COOR$^{14}$, or —(CH$_2$)$_n$COOH;
$R^{11}$ is selected from the group consisting of methyl, ethyl, propyl, butyl, pentyl, hexyl, and heptyl;
$R^{12}$ is —H;
$R^{13}$ is selected from the group consisting of (C$_1$-C$_{10}$) alkyl, (C$_1$-C$_{10}$)haloalkyl, (C$_3$-C$_{10}$)aryl, (C$_3$-C$_{10}$)cycloalkyl, (C$_3$-C$_{10}$)aryl-(C$_1$-C$_{10}$)alkylene, (C$_3$-C$_{10}$)cycloalkyl-(C$_1$-C$_{10}$)alkylene, —CH$_2$—CH$_2$—[O—CH$_2$—CH$_2$—]$_m$O—CH$_2$—CH$_2$—R$^b$, —(CHR$^a$)$_q$—NH$_2$, and —(CHR$^a$)$_q$—NH$^+_3$X$^-$;
$R^a$ is selected from the group consisting of —H, —OH, halogen, (C$_{1-5}$) alkyl, and alkoxy;
$R^b$ is selected from the group consisting of —OH, —O(C$_1$-$_5$) alkyl, —(C$_2$-C$_6$) alkene, azide, and —(C$_2$-C$_6$) alkyne;
$R^{14}$ is —H or (C$_1$-C$_{10}$) alkyl;
X is a counter ion derived from a pharmaceutically acceptable acid;
Z is a leaving group;
n, m and q are each independently 0, 1. 2, 3, 4, 5, 6, 7, 8, 9, or 10; and
wherein the biological concentration of the Formula IVa compound measured as the area under a curve of plasma concentration against time in a human subject, is in the range from about 2 ng/mL to 25 ng/mL per milligram of the Formula IVa compound administered to the subject.

21. A method for treating a neurological condition, comprising:
administering a therapeutically effective amount of a Formula V compound to a subject in need of treatment, Formula V

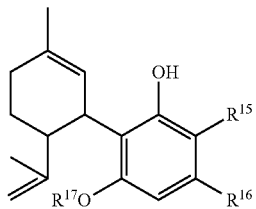

wherein
$R^{15}$ is —H, —COOR$^{18}$, or —(CH$_2$)$_n$COOH;
$R^{16}$ is selected from the group consisting of methyl, ethyl, propyl, butyl, pentyl, hexyl, and heptyl;
$R^{17}$ is selected from the group consisting of (C$_1$-C$_{10}$) alkyl, (C$_1$-C$_{10}$) haloalkyl, (C$_3$-C$_{10}$)aryl, (C$_3$-C$_{10}$)cycloalkyl, (C$_3$-C$_{10}$)aryl-(C$_1$-C$_{10}$)alkylene, (C$_3$-C$_{10}$)cycloalkyl—(C$_1$-C$_{10}$)alkylene, —CH$_2$—CH$_2$—[O—CH$_2$—CH$_2$—]$_m$O—CH$_2$—CH$_2$—R$^b$, —(CHR$^a$)$_q$—NH$_2$, and —(CHR$^a$)$_q$—NH$^+_3$X$^-$;
$R^a$ is selected from the group consisting of —H, —OH, halogen, (C$_1$-C$_5$) alkyl, and alkoxy;
$R^b$ is selected from the group consisting of —OH, —O(C$_1$-C$_5$) alkyl, —(C$_2$-C$_6$) alkene, azide, and —(C$_2$-C$_6$) alkyne;
$R^{18}$ is —H or (C$_1$-C$_{10}$) alkyl;
X is a counter ion derived from a pharmaceutically acceptable acid; and
n, m and q are each independently 0, 1, 2, 3, 4, 5, 6, 7, 8, 9, or 10,
wherein the neurological condition is selected from the group consisting of Alzheimer's disease, Parkinson's disease, dementia, and schizophrenia.

* * * * *